(12) United States Patent
Wersland et al.

(10) Patent No.: US 11,331,244 B2
(45) Date of Patent: May 17, 2022

(54) VIBRATION THERAPY SYSTEM AND DEVICE

(71) Applicant: Theragun, Inc., Beverly Hills, CA (US)

(72) Inventors: Jason Wersland, Manhattan Beach, CA (US); Benjamin Nazarian, Beverly Hills, CA (US); Jaime Sanchez Solana, Los Angeles, CA (US); Eduardo Merino, Beverly Hills, CA (US); Bill Webb, San Francisco, CA (US); Alex Zhu, Xiamen (CN)

(73) Assignee: THERABODY, INC., Los Angeles, CA (US)

( * ) Notice: Subject to any disclaimer, the term of this patent is extended or adjusted under 35 U.S.C. 154(b) by 0 days.

(21) Appl. No.: 17/361,966

(22) Filed: Jun. 29, 2021

(65) Prior Publication Data

US 2021/0401663 A1 Dec. 30, 2021

Related U.S. Application Data

(60) Provisional application No. 63/133,530, filed on Jan. 4, 2021, provisional application No. 63/065,348, filed
(Continued)

(51) Int. Cl.
*A61H 23/00* (2006.01)
*A61H 23/02* (2006.01)
(Continued)

(52) U.S. Cl.
CPC ............ *A61H 23/02* (2013.01); *A61N 1/328* (2013.01); *A61N 1/36014* (2013.01);
(Continued)

(58) Field of Classification Search
CPC ............ A61H 7/003; A61H 2201/0153; A61H 15/0085; A61H 23/00; A61H 23/006; A61H 15/02; A61N 1/328; A61N 5/0616
See application file for complete search history.

(56) References Cited

U.S. PATENT DOCUMENTS

| 1,955,863 A | 4/1934 | Schmidt |
| 2,183,726 A | 12/1939 | Sommer |

(Continued)

FOREIGN PATENT DOCUMENTS

| WO | 2019097291 | 5/2019 |
| WO | 2019150887 | 8/2019 |

(Continued)

OTHER PUBLICATIONS

International Search Report and Written Opinion issued in PCT/US21/39586.

*Primary Examiner* — Justine R Yu
*Assistant Examiner* — Christopher E Miller
(74) *Attorney, Agent, or Firm* — Jeffer Mangels Butler & Mitchell LLP; Brennan C. Swain, Esq.

(57) ABSTRACT

A vibration therapy device that includes a housing that includes a handle portion, a head portion and a module seat defined on the head portion, an electrical source, a motor positioned in the housing, a switch for activating the motor, a push rod assembly operatively connected to the motor and configured to reciprocate in response to activation of the motor, and a therapy module removably secured to the module seat. The distal end of the push rod assembly is configured to removably receive a reciprocating attachment thereon. The therapy module at least partially surrounds the distal end of the push rod assembly.

20 Claims, 16 Drawing Sheets

Related U.S. Application Data on Aug. 13, 2020, provisional application No. 63/045,365, filed on Jun. 29, 2020.

(51) Int. Cl.
  *A61N 5/06* (2006.01)
  *A61N 1/36* (2006.01)
  *A61N 1/32* (2006.01)

(52) U.S. Cl.
  CPC .... *A61N 5/0616* (2013.01); *A61H 2201/0153* (2013.01); *A61H 2201/105* (2013.01); *A61H 2201/1685* (2013.01); *A61N 2005/0626* (2013.01); *A61N 2005/0644* (2013.01); *A61N 2005/0651* (2013.01)

(56) References Cited

U.S. PATENT DOCUMENTS

| | | | |
|---|---|---|---|
| 4,858,600 A | 8/1989 | Gross | |
| 5,103,809 A | 4/1992 | DeLuca | |
| 6,535,761 B2 | 3/2003 | Bernabei | |
| 6,743,215 B2 | 6/2004 | Bernabei | |
| 6,748,266 B2 | 6/2004 | Bernabei | |
| 6,766,199 B2 | 7/2004 | Cook | |
| 6,980,854 B2 | 12/2005 | Bernabei | |
| 7,010,343 B2 | 3/2006 | Bernabei | |
| 7,014,639 B2 * | 3/2006 | Walneck | A61H 23/02 606/10 |
| 7,083,580 B2 | 8/2006 | Bernabei | |
| 7,204,832 B2 | 4/2007 | Altshuler | |
| 7,258,675 B2 | 8/2007 | Nichols | |
| 7,282,036 B2 | 10/2007 | Masuda | |
| 7,305,269 B2 | 12/2007 | Cook | |
| 7,376,460 B2 | 5/2008 | Bernabei | |
| 7,471,979 B2 | 12/2008 | Bernabei | |
| 7,532,926 B2 | 5/2009 | Bernabei | |
| 8,105,322 B2 | 1/2012 | Ely | |
| 8,157,753 B2 | 4/2012 | Nichols | |
| 8,182,473 B2 | 5/2012 | Altshuler | |
| 8,382,690 B2 | 2/2013 | Yoon | |
| 8,506,506 B2 | 8/2013 | Nebrigic | |
| 8,523,791 B2 | 9/2013 | Castel | |
| 8,540,702 B2 | 9/2013 | Ely | |
| D693,932 S | 11/2013 | Nichols | |
| 8,655,448 B2 | 2/2014 | Cook | |
| 8,696,605 B2 | 4/2014 | Nichols | |
| 8,906,009 B2 | 12/2014 | Nebrigic | |
| 8,945,104 B2 | 2/2015 | Boone, III | |
| 9,023,021 B2 | 5/2015 | Behrakis | |
| 9,042,993 B2 | 5/2015 | Cook | |
| 9,084,587 B2 | 7/2015 | Eckhouse | |
| D736,399 S | 8/2015 | Nichols | |
| 9,272,141 B2 | 3/2016 | Nichols | |
| 9,278,045 B2 | 3/2016 | Scerbo | |
| 9,386,837 B2 | 7/2016 | Geva | |
| D764,173 S | 8/2016 | Nichols | |
| D765,982 S | 9/2016 | Nichols | |
| 9,579,250 B2 | 2/2017 | Nichols | |
| 9,585,687 B2 | 3/2017 | Tenenbaum | |
| D803,572 S | 11/2017 | Nichols | |
| 9,808,646 B2 | 11/2017 | Piergallini | |
| 9,872,813 B2 | 1/2018 | Giraud | |
| 9,925,006 B2 | 3/2018 | Behrakis | |
| 10,016,337 B2 | 7/2018 | Roberts | |
| 10,124,165 B2 | 11/2018 | Gimelli | |
| 10,137,054 B2 | 11/2018 | Giraud | |
| 10,252,051 B2 | 4/2019 | Nichols | |
| 10,376,659 B2 | 4/2019 | Nichols | |
| 10,278,888 B2 | 5/2019 | Sabattier | |
| 10,285,722 B2 | 5/2019 | Favie | |
| 10,307,330 B1 | 6/2019 | Sedic | |
| 10,383,486 B2 | 8/2019 | Nichols | |
| 10,511,777 B2 * | 12/2019 | Nichols | A46B 15/0004 |
| 10,518,097 B2 | 12/2019 | Grez | |
| 10,625,093 B2 | 4/2020 | Shenfarber | |
| 10,661,072 B2 | 5/2020 | Kern | |
| 10,695,508 B2 | 6/2020 | Lorberbaum | |
| 10,737,107 B2 | 8/2020 | Ledany | |
| 10,821,299 B1 | 11/2020 | Shenfarber | |
| 10,881,577 B2 | 1/2021 | Hashimoto | |
| 2004/0030325 A1 | 2/2004 | Cahir | |
| 2004/0147984 A1 | 7/2004 | Altshuler | |
| 2005/0043653 A1 | 2/2005 | Trimmer | |
| 2007/0038206 A1 | 2/2007 | Altshuler | |
| 2007/0179573 A1 | 8/2007 | Laurent | |
| 2007/0198004 A1 | 8/2007 | Altshuler | |
| 2007/0213696 A1 | 9/2007 | Altshuler | |
| 2007/0213698 A1 * | 9/2007 | Altshuler | A46B 15/0036 606/12 |
| 2007/0239142 A1 | 10/2007 | Altshuler | |
| 2007/0239143 A1 | 10/2007 | Altshuler | |
| 2008/0014011 A1 | 1/2008 | Rossen | |
| 2008/0065176 A1 | 3/2008 | Zhang | |
| 2008/0119913 A1 | 3/2008 | Powell | |
| 2008/0103560 A1 | 5/2008 | Powell | |
| 2008/0103563 A1 * | 5/2008 | Powell | A61N 5/0616 607/89 |
| 2008/0125835 A1 | 5/2008 | Laurent | |
| 2008/0193493 A1 | 5/2008 | Rhoades | |
| 2008/0215123 A1 | 9/2008 | Maricle | |
| 2008/0275532 A1 | 11/2008 | Yamazaki | |
| 2009/0043293 A1 | 2/2009 | Pankratov | |
| 2009/0234338 A1 | 9/2009 | Roth | |
| 2009/0287195 A1 | 11/2009 | Altshuler | |
| 2010/0121419 A1 * | 5/2010 | Douglas | A61N 5/0616 607/90 |
| 2010/0137752 A1 * | 6/2010 | Heine | A61B 17/1697 601/2 |
| 2010/0274162 A1 * | 10/2010 | Evans | A61H 15/0092 601/15 |
| 2010/0274329 A1 * | 10/2010 | Bradley | A61N 1/328 607/90 |
| 2010/0312157 A1 | 12/2010 | Yan | |
| 2011/0040235 A1 * | 2/2011 | Castel | A61M 37/0092 604/20 |
| 2011/0106067 A1 * | 5/2011 | Geva | A45D 40/18 606/9 |
| 2011/0184499 A1 | 7/2011 | Radi | |
| 2012/0065555 A1 | 3/2012 | Chae | |
| 2012/0109041 A1 | 5/2012 | Munz | |
| 2012/0310124 A1 * | 12/2012 | Zhang | A61H 23/0263 601/46 |
| 2013/0012851 A1 | 1/2013 | Fahmie | |
| 2013/0046212 A1 * | 2/2013 | Nichols | A61H 7/005 601/18 |
| 2013/0060176 A1 | 3/2013 | Nichols | |
| 2014/0128780 A1 * | 5/2014 | Kennedy | A61B 17/12131 601/18 |
| 2014/0135798 A1 | 5/2014 | David | |
| 2014/0219701 A1 | 8/2014 | Eberlein | |
| 2014/0276255 A1 * | 9/2014 | McGushion | A61H 7/007 601/17 |
| 2014/0288364 A1 | 9/2014 | St. Bernard | |
| 2014/0323927 A1 | 10/2014 | Kim | |
| 2014/0336540 A1 | 11/2014 | Chen | |
| 2014/0371637 A1 * | 12/2014 | Lee | A61H 23/0245 601/2 |
| 2014/0378555 A1 | 12/2014 | Hung | |
| 2015/0045702 A1 | 2/2015 | Lin | |
| 2015/0100002 A1 | 4/2015 | Choi | |
| 2015/0119771 A1 * | 4/2015 | Roberts | A61N 1/26 601/135 |
| 2015/0224020 A1 | 8/2015 | Flyash | |
| 2015/0265825 A1 * | 9/2015 | Miller | A61N 1/325 604/20 |
| 2015/0283025 A1 | 10/2015 | Ledany | |
| 2015/0297393 A1 * | 10/2015 | McGushion | A61H 7/005 601/15 |
| 2015/0305969 A1 | 10/2015 | Giraud | |
| 2016/0184162 A1 * | 6/2016 | Grez | A61F 7/007 601/18 |
| 2016/0324719 A1 | 11/2016 | Badmus | |

(56) References Cited

U.S. PATENT DOCUMENTS

| | | | |
|---|---|---|---|
| 2017/0049278 A1 | 2/2017 | Thomassen | |
| 2017/0056685 A1 | 3/2017 | Harvey | |
| 2017/0072175 A1 | 3/2017 | Batiste | |
| 2017/0128130 A1 | 5/2017 | Giraud | |
| 2017/0189670 A1* | 7/2017 | Brunson | A61H 7/001 |
| 2017/0202732 A1 | 7/2017 | Nichols | |
| 2017/0238686 A1 | 8/2017 | Sanchez Martinez | |
| 2018/0015299 A1 | 1/2018 | Kawa | |
| 2018/0031089 A1* | 2/2018 | Wong | F16H 25/186 |
| 2018/0031090 A1* | 2/2018 | Wong | A61H 23/004 |
| 2018/0133470 A1 | 5/2018 | Park | |
| 2018/0168318 A1* | 6/2018 | Streeter | A45D 40/261 |
| 2018/0185236 A1 | 7/2018 | Levi | |
| 2019/0240110 A1 | 8/2019 | Sedic | |
| 2019/0254922 A1 | 8/2019 | Marton | |
| 2019/0262607 A1 | 8/2019 | Nichols | |
| 2019/0343712 A1 | 11/2019 | Cheng | |
| 2019/0388707 A1* | 12/2019 | Shenfarber | A61N 5/0625 |
| 2020/0038673 A1 | 2/2020 | Yildirim | |
| 2020/0086137 A1 | 3/2020 | Yoo | |
| 2020/0093945 A1* | 3/2020 | Jeong | H04R 1/028 |
| 2020/0113322 A1 | 4/2020 | Balestrini | |
| 2020/0129372 A1 | 4/2020 | Tseng | |
| 2020/0179220 A1* | 6/2020 | Jablow | A61H 1/00 |
| 2020/0215351 A1 | 7/2020 | Shenfarber | |
| 2020/0237085 A1 | 7/2020 | Miller | |
| 2020/0237604 A1 | 7/2020 | Truong | |
| 2020/0253811 A1 | 8/2020 | Alexander | |
| 2020/0268594 A1 | 8/2020 | Pepe | |
| 2020/0280680 A1 | 9/2020 | Nichols | |
| 2020/0288843 A1 | 9/2020 | Verheem | |
| 2020/0352306 A1* | 11/2020 | Um | A61L 2/26 |
| 2020/0352317 A1* | 11/2020 | Yeates | A46B 15/0016 |
| 2020/0390468 A1 | 12/2020 | Alexander | |
| 2021/0001148 A1 | 1/2021 | Verheem | |
| 2021/0128402 A1* | 5/2021 | Dai | A61H 23/0263 |

FOREIGN PATENT DOCUMENTS

| | | |
|---|---|---|
| WO | 2019155210 A2 | 8/2019 |
| WO | 2020028329 | 2/2020 |
| WO | 2020154177 | 7/2020 |
| WO | 2020159727 | 8/2020 |
| WO | 2020163738 | 8/2020 |
| WO | 2020252440 | 12/2020 |

* cited by examiner

VIBRATION THERAPY SYSTEM AND DEVICE

CROSS REFERENCE TO RELATED APPLICATIONS

This application claims the benefit of U.S. Provisional Application No. 63/133,530, filed Jan. 4, 2021, U.S. Provisional Application No. 63/065,348, filed Aug. 13, 2020, and U.S. Provisional Patent Application No. 63/045,365, filed Jun. 29, 2020, the entireties of which are incorporated by reference herein.

FIELD OF THE INVENTION

The present invention relates generally to a vibration therapy system and device, and more particularly to a vibration therapy device with interchangeable attachments.

BACKGROUND OF THE INVENTION

As people age, devices for skin and facial care are needed. Percussive massage devices that provide reciprocating motion and provide relief to sore muscles and other parts of the body are known. For example, see U.S. Pat. Nos. 10,857,064 and 10,945,915, the entireties of which are incorporated by reference herein. However, many percussive massage devices may be uncomfortable if used on the face and principally target the underlying muscles. The present invention addresses the needs discussed herein.

The background description disclosed anywhere in this patent application includes information that may be useful in understanding the present invention. It is not an admission that any of the information provided herein is prior art or relevant to the presently claimed invention, or that any publication specifically or implicitly referenced is prior art.

SUMMARY OF THE PREFERRED EMBODIMENTS

In accordance with a first aspect of the present invention there is provided a vibration therapy device that includes a housing that includes a handle portion, a head portion and a module seat defined on the head portion, an electrical source, a motor positioned in the housing, a switch for activating the motor, a push rod assembly operatively connected to the motor and configured to reciprocate in response to activation of the motor, and a therapy module removably secured to the module seat. The distal end of the push rod assembly is configured to removably receive a reciprocating attachment thereon. The therapy module at least partially surrounds the distal end of the push rod assembly. In a preferred embodiment, the push rod assembly includes an attachment member that defines the distal end of the push rod assembly. The therapy module is coaxial with the distal end of the push rod assembly (e.g., the attachment member and/or the magnet seat), and at least a portion of the attachment member (e.g., the magnet member) extends into the therapy module.

In a preferred embodiment, the therapy module is in electrical communication with the electrical source (so that it can be powered) and/or is in data communication with the controller/processor of the device (so that it can be operated as desired). For electrical connection, the module seat preferably includes a first electrical connector (male or female), and wherein the therapy module includes a second electrical connector (female or male) in electrical communication with the first electrical connector. The therapy module may comprise a ring module that includes a central opening and an outer surface. When a reciprocating attachment that includes a contact surface is removably received on the distal end of the push rod assembly, the contact surface of the reciprocating attachment extends further from the module seat than the outer surface of the ring module.

The therapy module may be a ring module that includes a plurality of LED's therein or thereon. The LEDs are configured to operate at a treatment level only when the outer surface is less than a predetermined distance from an operating surface. In a preferred embodiment, the ring module further includes at least first and second proximity sensors that are positioned approximately 180° from one another within the ring module (e.g. on the PCB). The first and second proximity sensors are each configured to activate the LEDs at the treatment level when the outer surface of the ring module is less than the predetermined distance from the operating surface.

The therapy module may comprise a cap module that includes a main body portion and a rear recess and where at least a portion of the attachment member extends into the rear recess. The cap module may include an anode and a cathode and may be configured to provide micro-current therapy. The cap module may also be configured to be removably secured to the module seat and the attachment member. In this embodiment, the cap module may be removably secured to the module seat via magnets and/or one or more securement protrusions and recesses (that also help properly align the cap module).

In accordance with another aspect of the invention there is provided a vibration therapy system that includes a vibration therapy device, a ring module that includes a central opening and that is configured to be removably secured to the module seat, a cap module that includes a main body portion and a rear recess and that is configured to be removably secured to the module seat, and a reciprocating attachment that is configured to be removably received on the attachment member. When the ring module is removably secured to the module seat, the distal end of the push rod assembly extends into the central opening. When the cap module is removably secured to the module seat, the distal end of the push rod assembly extends into the rear recess. When the ring module is received on the module seat, the reciprocating attachment extends through the central opening. When the ring module is received on the module seat the attachment member can be reciprocated, and when the cap module is received on the module seat the attachment member cannot be reciprocated.

In accordance with another aspect of the invention there is provided a vibration therapy device that includes a housing that includes a handle portion and a head portion an electrical source, a motor positioned in the housing, a switch for activating the motor, a push rod assembly operatively connected to the motor and configured to reciprocate in response to activation of the motor, and a reciprocating attachment removably secured to a distal end of the push rod assembly. The reciprocating attachment includes a contact surface, and a skin treatment member is removably secured to the reciprocating attachment such that a delivery portion at least partially covers the contact surface. In a preferred embodiment, the reciprocating attachment includes a groove defined therein and at least a portion of the skin treatment member is received in the groove. Preferably, the skin treatment member includes a main body portion that, together with the delivery portion, defines an attachment recess. At least one ridge member extends inwardly from the main body portion into the attachment recess and is received in the groove on the reciprocating attachment. In a preferred embodiment, the delivery portion includes a lotion or other formulation thereon.

Described herein is a vibration therapy device that includes interchangeable attachments that provide therapy to a user. The interchangeable attachments can include, for example, LED light therapy, micro-current, etc. Generally, the present invention is a vibration therapy device that includes LED lights thereon that can be used for skin therapy. LED skin therapy is known. For example, see U.S. Pat. Nos. 6,524,329 and 6,974,224, the entireties of which are incorporated by reference herein.

The present invention is a hand-held vibration facial massager or vibration therapy device that includes different therapy attachments compatible therewith. The hand-held device, which is intended to be used on the face, but can also be used anywhere else on the body, combines vibration therapy with other facial treatment technologies, including, but not limited to, LED light therapy, micro-current treatments and radio frequency skin technology.

As discussed below, the vibration therapy treatment can be delivered by a brushless motor-drive train system with the distal end of the reciprocating output shaft including an amplitude of preferably between 2.0 mm and 8.0 mm. It will be appreciated that this small amplitude of reciprocation is referred to herein as a vibrating movement or vibration, hence the phrase "vibration therapy device." However, the amplitude can be anywhere between 1.0 mm and 25 mm. The removable or interchangeable vibration therapy attachment on the end of the output shaft can be any type of attachment (see, e.g., the patents discussed above). In a preferred embodiment, the attachment is a foam/rubber attachment that is connected to the end of the shaft to deliver the vibration to the user's face. See, e.g., U.S. Pat. No. 10,758,452, the entirety of which is incorporated by reference herein.

The present invention includes an attachment system to accommodate swappable or interchangeable rings or modules with different facial treatment technologies. For example, the module can be a blue, red, amber and/or infrared LED light therapy light ring module or can be a module that includes micro-current therapy, RF (radio frequency) therapy, heat, cold, electric stimulation and/or vibration (e.g., the therapy module can include one or more motors or the like that provide vibration, separate from the reciprocation of the reciprocating attachment). As discussed below, in a preferred embodiment, the device includes an electrical connection system to deliver electric power to the ring or module and a magnet-based system to secure the ring or module in place.

In one preferred embodiment, the magnets are programmed or polymagnets. Polymagnets are magnetic structures that incorporate correlated patterns of magnets with alternating polarity, designed to achieve a desired behavior and deliver stronger local force. By varying the magnetic fields and strengths, different mechanical behaviors can be controlled. Correlated magnet pairs can be programmed to attract or repel with a prescribed force and engagement distance, or, to attract or repel at a certain spatial orientation. Correlated magnets can be programmed to interact only with other magnetic structures that have been coded to respond. As a result, a strong force can be used to hold the module on the device, but a fairly weak force can be used for removing the module. For example, the user can rotate the module about the module's central axis to a predetermined point where the module can be easily removed. The polymagnets in the device can even repel the polymagnets in the module at a certain rotation point, thus making removal of the module very easy. The polymagnets change properties based on the distance and position of the magnets in the ring module and the device with respect to one another. This allows the locking and unlocking forces that the user needs to apply to connect and disconnect the module from the device to be reduced compared to the use of regular magnets. For example: the magnets can repel each other when the distance between them is more than one inch but if they are brought closer than one inch they attract each other. Therefore, for example, at a first distance and a first degree of rotation, the force required to secure the module or push the module into place on the module seat (referred to herein as "attach the module") is X and at the first distance and a second degree of rotation, the force required to attach the module is Y, where Y is less than X. To detach the module or pull it off the device, the force required may be A at a first set of degrees of rotation and B at a second set of degrees of rotation, where A is less than B. For example, the first set of degrees of rotation may be 0° to 15° and the second set of degrees of rotation may be 16° to 360°. Therefore, when the module or attachment is rotated to an angle between 0° to 15° it is easy to remove. At any other angle it is difficult for the user to remove.

In a preferred embodiment, the device and/or system also includes a software application downloadable to a portable electronic device that includes the ability to control the treatment and build different protocols via Bluetooth and the like.

In a preferred embodiment, the device and/or the therapy module includes a proximity sensor that detects the distance between the device and the user's face so that the therapy or treatment can be modified accordingly. For example, the light ring module can include one or more proximity sensors so that the LED lights can be dimmed and/or turned off when the device is pulled away from the user's skin and is not within a predetermined distance (i.e., when the ring is far enough from the user's face that no treatment is being provided). This may be done to save battery, for eye safety purposes or for other skin safety issues or concerns.

In a preferred embodiment, the handle forms an angle of about 120 degrees with the attachment arm or output shaft to avoid blocking the user's view during treatment. In a preferred embodiment, the housing includes a female charging jack for receiving a male connector and charging the battery. The device also includes one or more buttons or switches for controlling the device (e.g., on/off, speed control, change color of LEDs, etc.) and LEDs that provide indication of different functions, such as battery power or speed setting, etc.

In a preferred embodiment, the vibration therapy device includes a motor, battery, housing, and push rod assembly with a reciprocating shaft. The reciprocating shaft includes a male or female attachment member on the end thereof to which a massage or vibration attachment (that includes a corresponding female or male attachment member thereon) can be attached. In a preferred embodiment, the massage attachment is secured to the vibration therapy device using magnets. When the device is used with a ring module or attachment vibration attachment extends through the center of the ring. Any type of attaching or securing arrangement between the massage attachment and the vibration therapy device is within the scope of the invention. In a preferred embodiment, the amplitude is between about 2 mm and about 8 mm, which is smaller than many percussive massage devices. However, in another embodiment, the amplitude can be greater and between 1 mm and 26 mm or more.

In a preferred embodiment, the motor converts power from the power source into motion. In some embodiments, the motor is an electric motor. The electric motor may be any type of electric motor known in the art, including, but not limited to, a brushed motor, a brushless motor, a direct current (DC) motor, an alternating current (AC) motor, a mechanical-commutator motor, an electronic commutator motor, or an externally commutated motor. In a preferred embodiment, the motor is a brushless direct-current (BLDC) motor. Preferably, the percussive massage device includes a voltage-sensing resistor electrically coupled to the BLDC motor and a controller.

In a preferred embodiment, the vibration therapy device includes a removable light ring therapy module that surrounds the massage or reciprocating attachment. In a preferred embodiment, the light ring module includes a plurality of lights (e.g., LED's). Preferably, the light ring module is electrically connected to the vibration therapy device when it is attached thereto so that the battery powers the lights. The light ring module includes a central opening that at least partially surrounds the reciprocating attachment.

In a preferred embodiment, a plurality of different ring modules are included either separately or sold as a kit with the vibration therapy device. For example, separate ring modules can include lights with different wavelengths (e.g., red LEDs on one ring and blue LEDs on another). In another embodiment, lights with different wavelengths can be included on the same ring (e.g., blue and red LEDs on the same ring). The rings are interchangeable. The rings can be different sizes. Each of the ring modules can provide different functions or features. Some of the features can be used in conjunction with the vibration therapy massage attachment and others can be used with a massage attachment attached to the device. For example, the ring modules can include (either individually or in combination) heat, vibrations, electrodes for electrolysis and/or emitting electromagnetic pulses. As a result, the main device acts as a power source for powering all of the different ring modules and the therapy modules that cover the attachment member where the reciprocating attachment is seated. Therefore, the connected ring module can be used in conjunction with the reciprocating attachment or without the reciprocating attachment (e.g., with the attachment removed), so the outer surface of the ring module can be placed against the user's skin, if necessary for the type of treatment being administered.

In another embodiment, the LEDs and/or one or more of any of the other treatments or discussed herein (e.g., micro-current, temperature, cleansing, etc.) can be part of the vibration therapy device and not removable. In a preferred embodiment, the control center or user interface includes an up button, a down button and a select button, which can be used for scrolling or toggling through various modes, going up or down in intensity or mode and selecting the modes or modules or turning different functions (vibration, light, micro-current, etc.) on or off.

It will be appreciated that the vibration therapy device together with the therapy module and reciprocating attachment may be referred to herein as a vibration therapy system.

In a preferred embodiment, the light ring module (or other ring module) includes alignment or securement recesses defined in a rear side thereof that receive the securement protrusions. Magnet members are positioned in the ring and adjacent the securement recesses. It will be appreciated that the magnet members associated with the securement recesses are magnetically attracted to the securement protrusions.

In a preferred embodiment, the motor is preferably attached to a motor mount bracket that secures the motor to the housing. Preferably, the motor mount bracket includes a middle member having first and second opposite sides. The motor is positioned on the first side and the eccentric weight is positioned on the second side of the middle member. The push rod assembly comprises an L-shaped or curved connector or push rod (connected to the eccentric weight) and the reciprocating shaft (with pivotal connections therebetween). The middle member includes a shaft opening defined therein. The motor includes a rotatable motor shaft extending therefrom that extends from the first side of the middle member, through the shaft opening and to the second side of the middle member. In a preferred embodiment, the motor mount bracket includes a battery bracket portion extending therefrom that secures the battery in place.

Generally, when the therapy module is attached, the head portion of the vibration therapy device includes two concentric attachment rings, the inner one for the reciprocation or massage attachment (e.g., silicone vibration head) and the outer one for the therapy modules (e.g., LED, Micro-current etc.). In a preferred embodiment, the male attachment also includes magnets for attachment (or similar attachment mechanism) and can also include an electrical connection similar to the outer ring. Therefore, a single attachment that covers both the outer and inner part can be used that attaches to male attachment and securement protrusions, for example to accommodate more LEDs.

In another preferred embodiment, the reciprocating attachment can includes hooks for securing a microfiber material on the reciprocating attachment that can be used on the user's face or other body part for the vibration therapy treatment. The microfiber material is secured on both sides and under the reciprocating attachment and stretches across the top contact surface of the reciprocating attachment. The microfiber material can include lotion therein for treating the persons' skin.

It will be appreciated that different types of massage or reciprocating attachments can be used on the vibration therapy device. As discussed herein, one or more of the reciprocating attachments can include a groove extending therearound for attachment of a treatment member (for treating the user's skin). Another massage attachment can include a cone portion or be cone shaped. Another massage attachment can include a soft portion and a harder portion that are connected by velcro. Another massage attachment can include a plurality of spikes or needles that provide a microneedling type treatment.

It will be appreciated that all components and feature on the different embodiments shown herein are interchangeable with the components and features of any of the other embodiments discloses herein.

BRIEF DESCRIPTION OF THE DRAWINGS

Like numerals refer to like parts throughout the several views of the drawings.

DETAILED DESCRIPTION OF THE PREFERRED EMBODIMENTS

Figure 1:
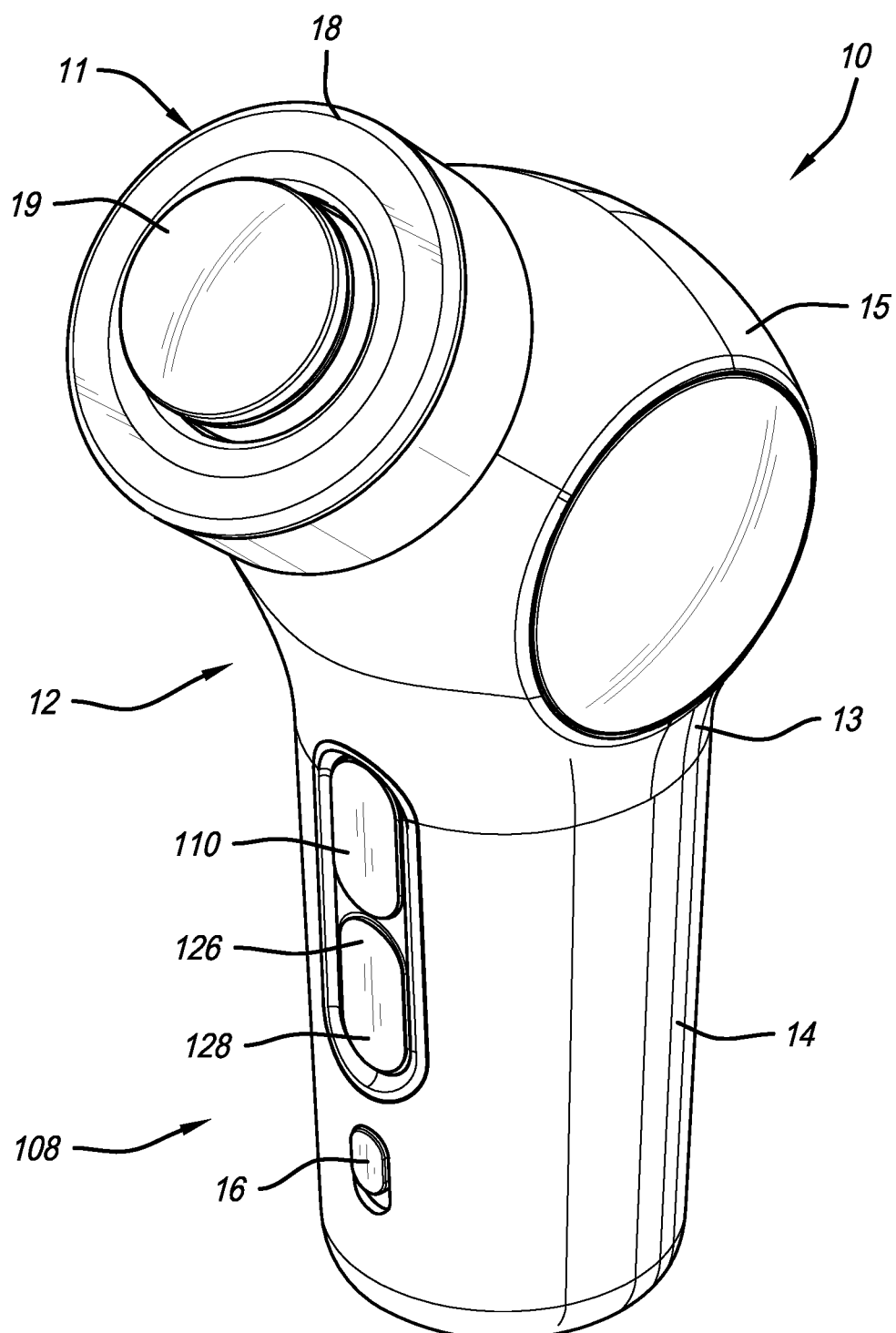
FIG. 1 is a perspective view of a vibration therapy system and device in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments. If a component is not shown in a drawing then this provides support for a negative limitation in the claims stating that that component is "not" present. However, the above statement is not limiting and in another embodiment, the missing component can be included in a claimed embodiment.

Reference in this specification to "one embodiment," "an embodiment," "a preferred embodiment" or any other phrase mentioning the word "embodiment" means that a particular feature, structure, or characteristic described in connection with the embodiment is included in at least one embodiment of the disclosure and also means that any particular feature, structure, or characteristic described in connection with one embodiment can be included in any embodiment or can be omitted or excluded from any embodiment. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others and may be omitted from any embodiment. Furthermore, any particular feature, structure, or characteristic described herein may be optional. Similarly, various requirements are described which may be requirements for some embodiments but not other embodiments. Where appropriate any of the features discussed herein in relation to one aspect or embodiment of the invention may be applied to another aspect or embodiment of the invention. Similarly, where appropriate any of the features discussed herein in relation to one aspect or embodiment of the invention may be optional with respect to and/or omitted from that aspect or embodiment of the invention or any other aspect or embodiment of the invention discussed or disclosed herein.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted.

It will be appreciated that the same thing can be said in more than one way. Consequently, alternative language and synonyms may be used for any one or more of the terms discussed herein. No special significance is to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," "aft," "forward," "inboard," "outboard" and "below" used herein are merely for ease of description and refer to the orientation of the components as shown in the figures. It should be understood that any orientation of the components described herein is within the scope of the present invention.

Referring now to the drawings, which are for purposes of illustrating the present invention and not for purposes of limiting the same, the drawings show a vibration therapy system 10 that includes a vibration therapy device 12, one or more reciprocating attachments 19 and one or more therapy modules 11. The reciprocating attachments can have different shapes. The therapy modules 11 can have different shapes and include different types of therapy, such as light, micro-current, heat, cold, vibration, etc.

Figure 2:
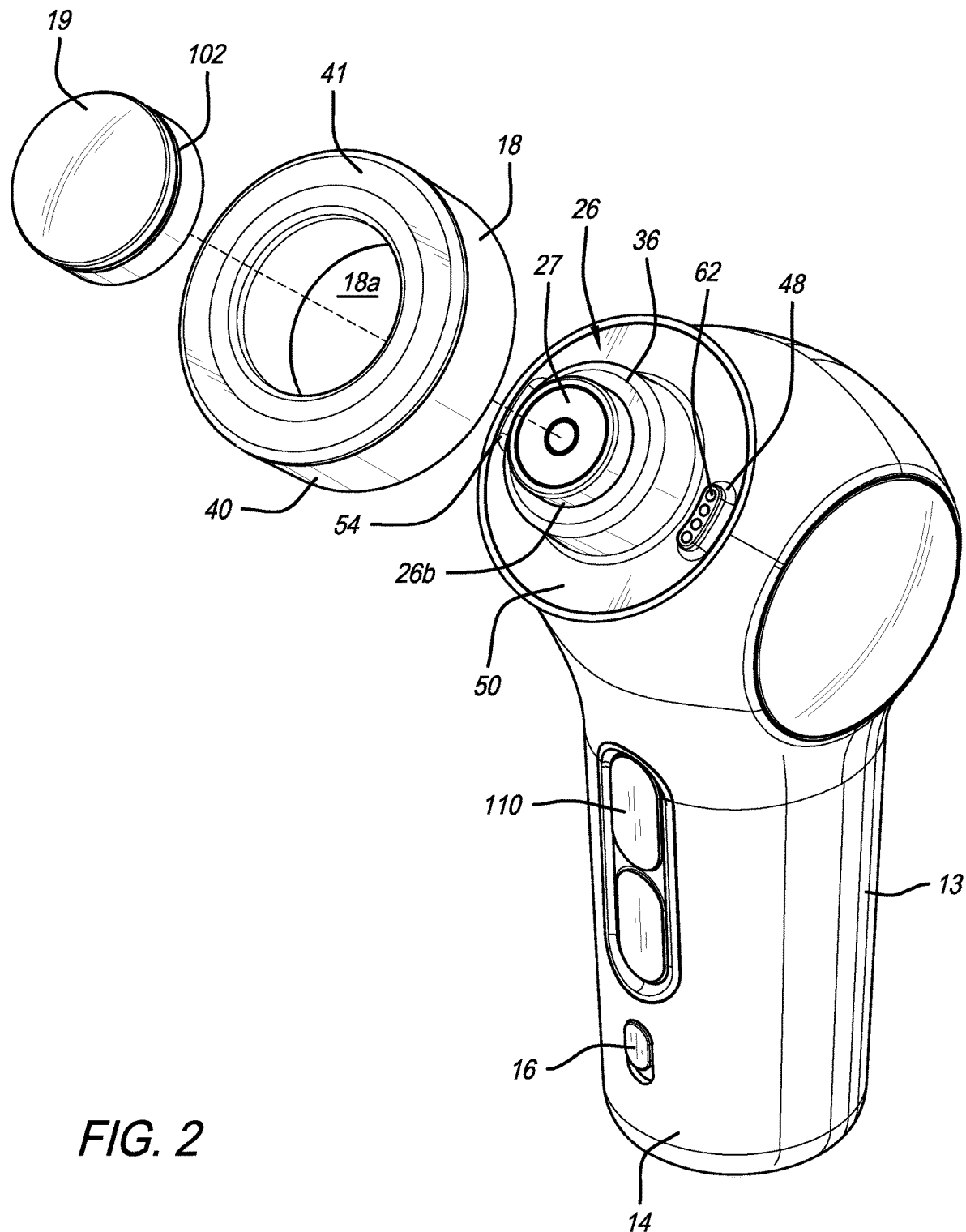
FIG. 2 is a perspective view of the vibration therapy device with the therapy module and reciprocating attachment exploded therefrom.
Figure 3:
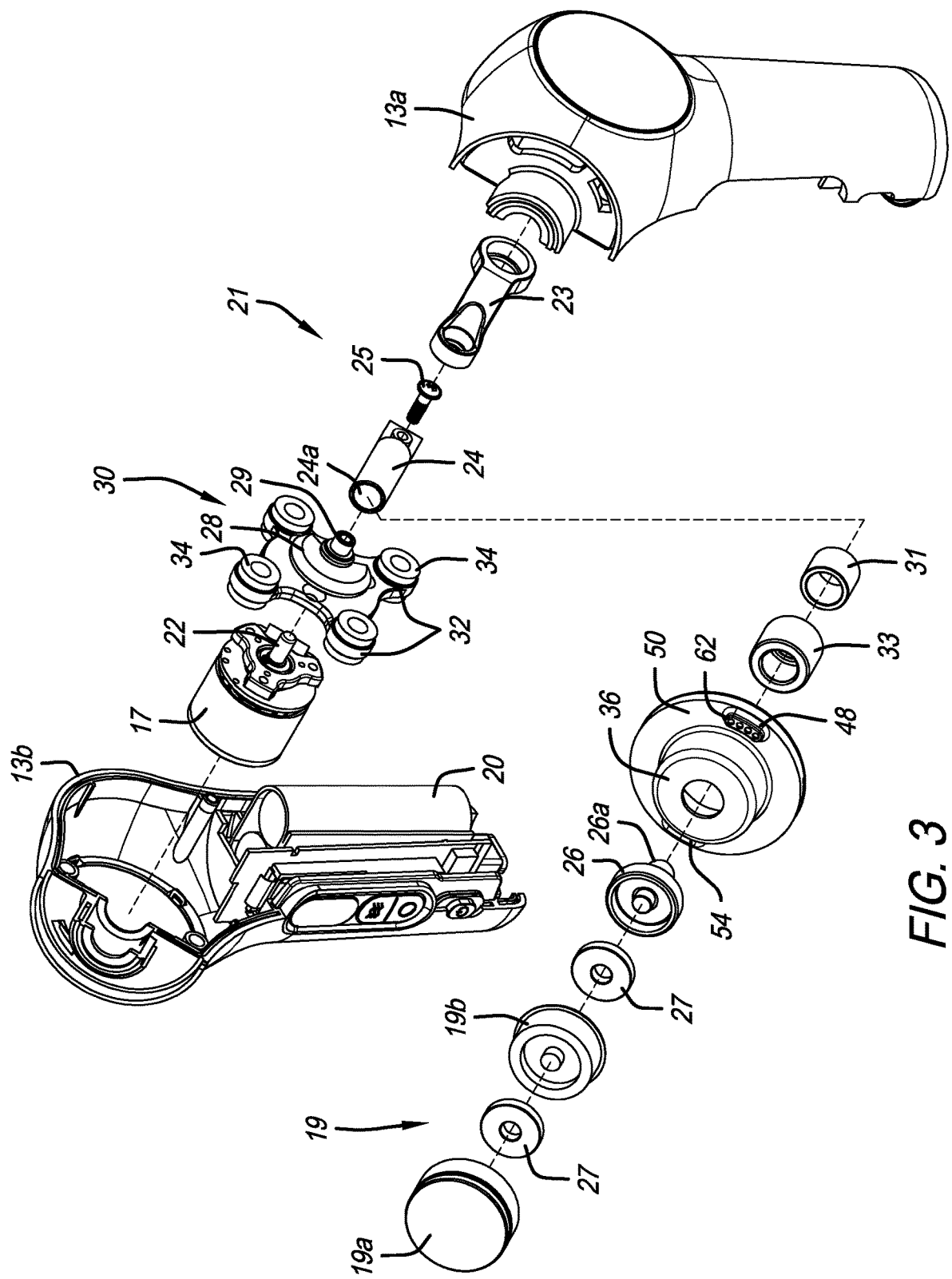
FIG. 3 is an exploded view of the vibration therapy device.

As shown in FIGS. 1-3, generally the vibration therapy device includes a housing 13 (two housing halves 13a and 13b are shown in FIG. 3), a handle portion 14, a head portion 15 and a switch 16 for activating the motor 17. FIGS. 1-8 show the vibration therapy device 12 with a therapy module 11 that is referred to herein as a ring module 18 (due to its shape with a central opening 18a) and a reciprocating attachment 19. As shown in FIG. 3, in a preferred embodiment, the vibration therapy device 12 includes an electrical source, such as a battery 20, positioned in the handle portion 14, the motor 17 positioned in the head portion 15, and a push rod assembly 21 operatively connected to the motor 17 and configured to reciprocate in response to activation of the motor 17.

Figure 4:
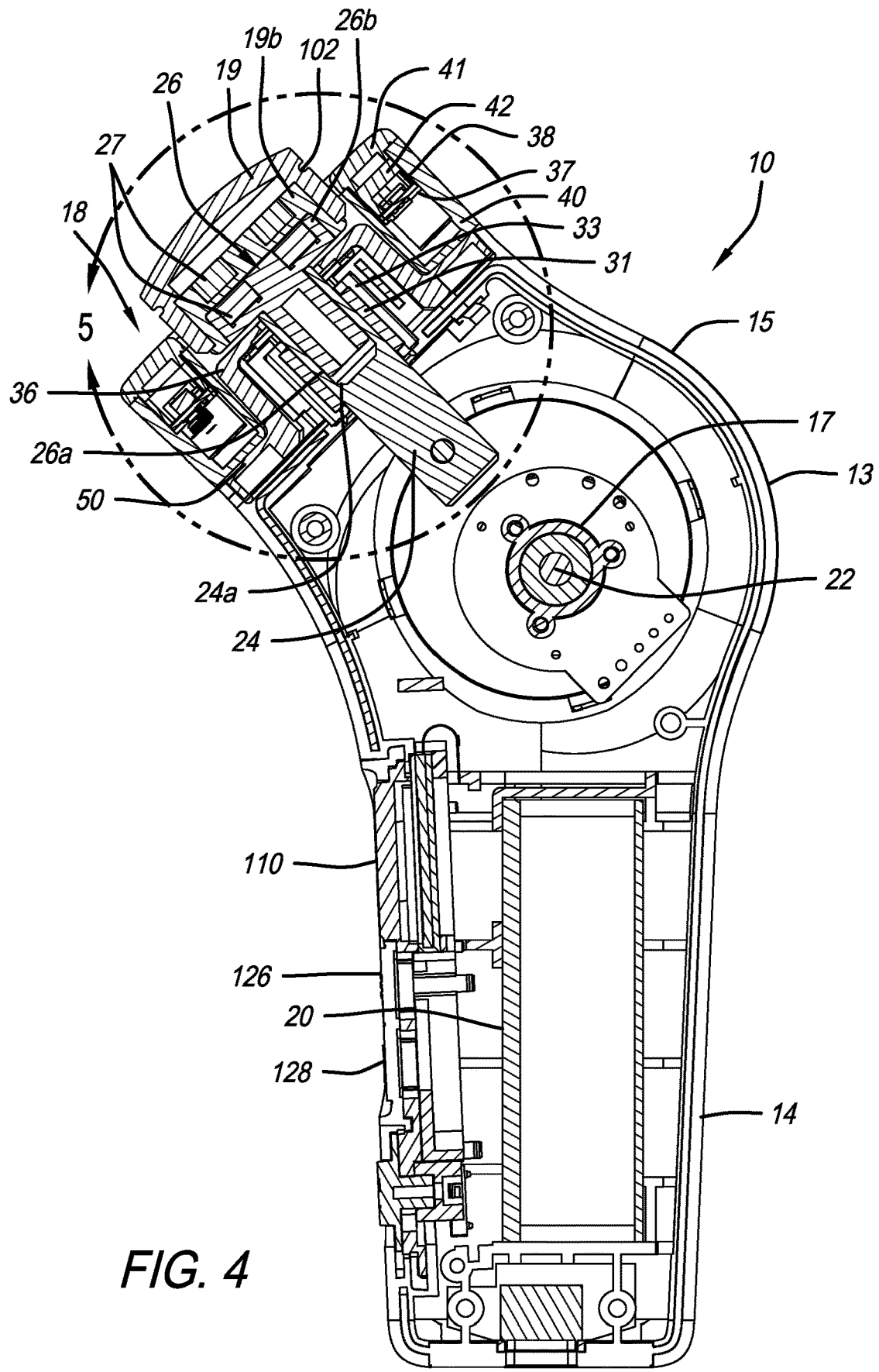
FIG. 4 is a cross-sectional view of the vibration therapy device.
Figure 5:
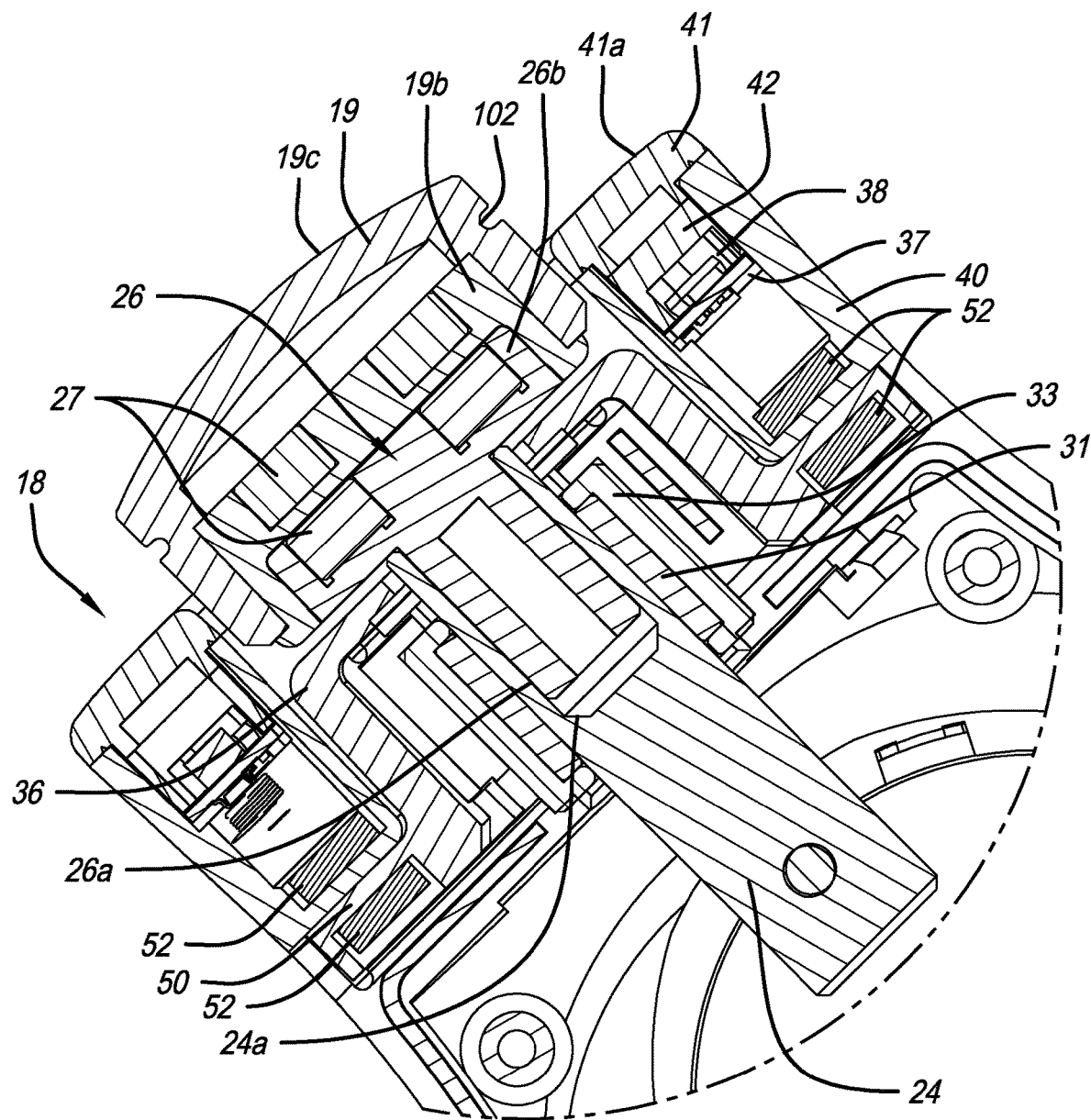
FIG. 5 is a cross-sectional view of a portion of the vibration therapy device taken along 5—5 of FIG. 4.

In a preferred embodiment, the rotation of the motor shaft 22 is converted to reciprocating motion of the push rod assembly 21. As shown in FIGS. 3-5, in a preferred embodiment, the push rod assembly 21 includes a push rod 23 that is pivotably connected to a reciprocating shaft 24 (see pivot pin 25), and an attachment member 26 that is operatively connected to the reciprocating shaft 24. In a preferred embodiment, the shaft 26a of the attachment member extends into and is connected within (via threads, friction fit, interference fit, etc.) an opening 24a defined in the reciprocating shaft 24. The distal end of the attachment member 26 (which is also the distal end of the push rod assembly 21) removably receives the reciprocating attachment 19. It will be appreciated that the term push rod assembly used herein includes any of the drive train components discussed herein or combinations thereof, e.g., push rod 23, reciprocating shaft 24 and attachment member 26 or the like that provide reciprocating motion and include the reciprocating attachment on the distal end thereof. The push rod assembly also includes the attachment member 26 (and any related components, such as the magnet described below) or any other connector at the end of the reciprocating components that allows connection of a reciprocating attachment to be used for massage or therapy.

Preferably, the drive train also includes a counterweight member 28 between the motor shaft 22 and the push rod 23. The motor shaft 22 is received in an opening in the counterweight member 28 and an offset shaft 29 extends from the counterweight member 28 and is received in an opening in the push rod 23. The reciprocating shaft 24 extends through the bush 31 and bush holding structure 33.

In a preferred embodiment, the motor 17 is secured to a motor mount 30 that includes a plurality of feet 32 that are secured to the housing 13 via threaded fasteners or the like that extend through openings in the feet 32. Dampening rings 34 and dampening washers can also be included. All dampening components herein are made of rubber, silicone or the like and are provided to prevent plastic to plastic or plastic to metal contact and to reduce noise and vibration.

In a preferred embodiment, the attachment member 26 includes the shaft 26a and a magnet seat 26b. The magnet seat 26b includes a magnet 27 received therein or otherwise operatively associated therewith. As shown in FIG. 3, the housing 13 includes a cap portion 35 that includes the module seat 50 and a protrusive portion 36. The attachment member 26 extends through an opening in the cap portion such that the magnet seat 26b is located outside of the housing 13, and particularly, the protrusive portion 36 of the housing 13. As described above, the distal end of the attachment member 26 (the magnet seat 26b) removably receives the reciprocating attachment 19. In a preferred embodiment, the magnet 27 in the attachment member is magnetically attracted to a magnet 27 in the reciprocating attachment 19 or other component placed on the attachment member 26. FIG. 3 shows an exemplary reciprocating attachment 19 including the main body portion 19a, inner support portion 19b and magnet 27.

Figure 6:
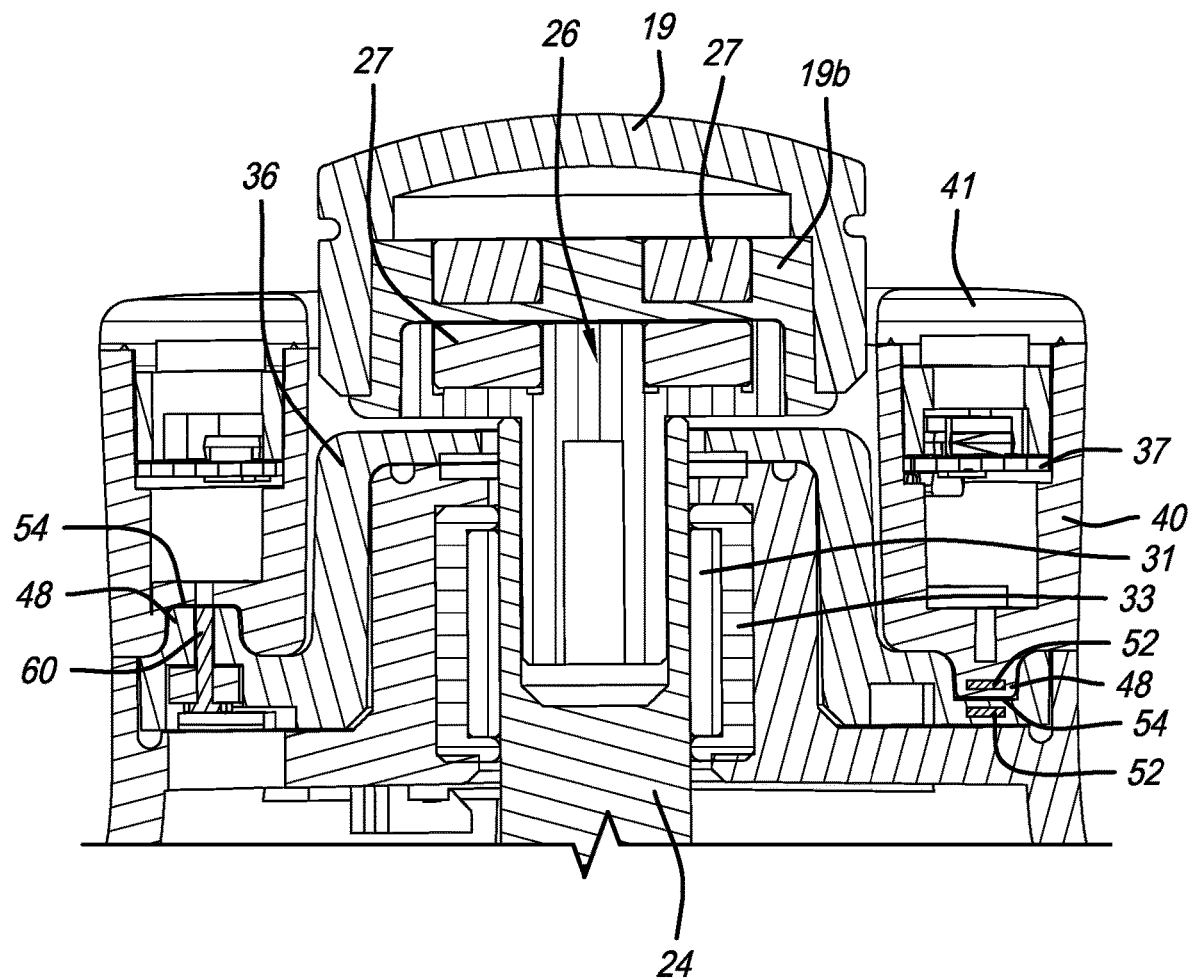
FIG. 6 is a cross-sectional view of a portion of the vibration therapy device showing the securement protrusions and securement recesses with the electrical connection and magnetic connection.

As shown in FIG. 2, in a preferred embodiment, the head portion 15 includes a module seat 50 that removably receives the therapy modules 11. As shown in FIG. 6, the vibration therapy system 10 includes an attachment system 44 for properly aligning or mounting and attaching or securing the various therapy modules 11 on the module seat 50, as well as providing electrical connection or communication (if needed) between the therapy modules 11 and the vibration therapy device 12. In a preferred embodiment, the attachment system 44 includes magnetic attraction between the module seat 50 and therapy module 11 and includes one or more complementary securement protrusions 48 and securement recesses 54 extending or protruding from the module seat 50 and/or the back of the therapy module 11. The securement protrusions are received in the securement recesses. The attachment system 44 provides the ability to accommodate the swappable or interchangeable therapy modules 11 (e.g., ring module 18) with different facial treatment technologies.

Figure 7:
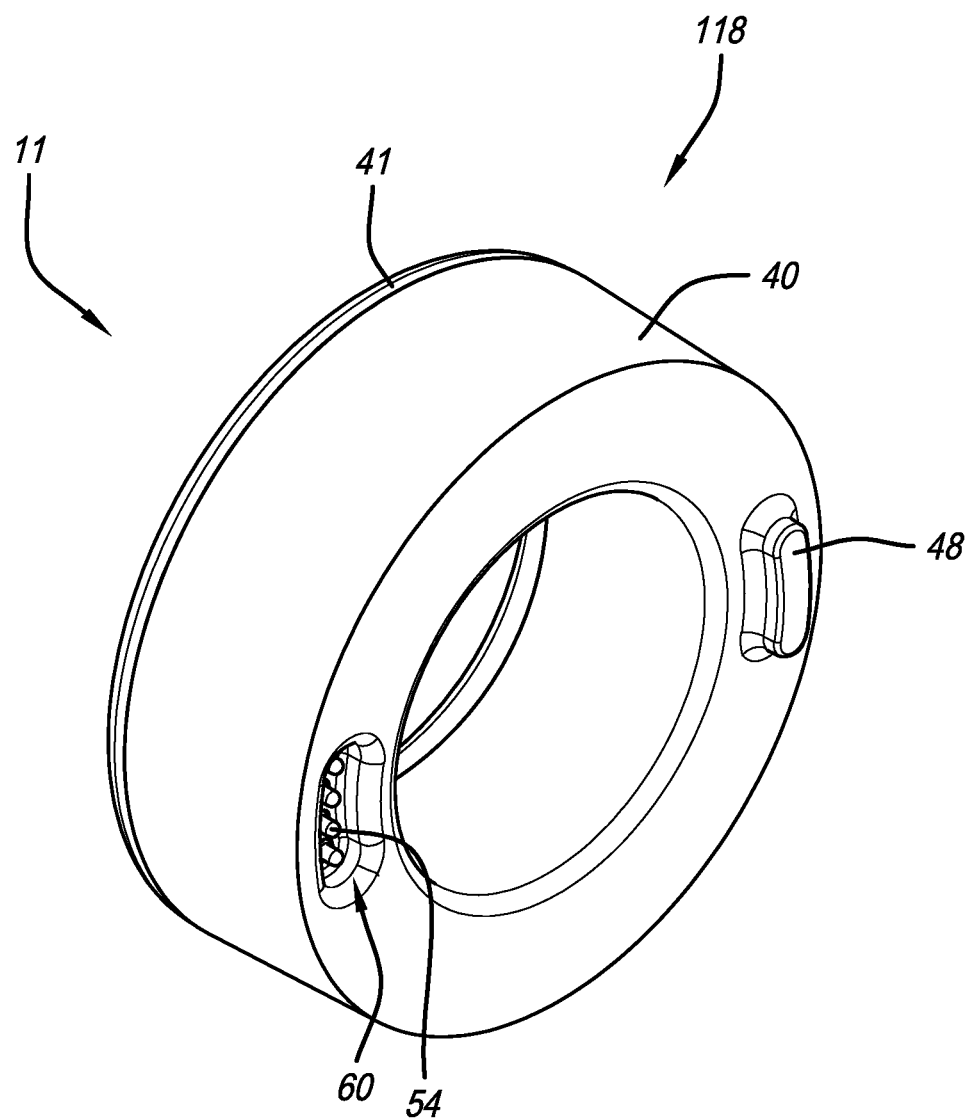
FIG. 7 is a rear perspective view of the light ring module.

As shown in FIGS. 6-7, in a preferred embodiment, one securement protrusion 48 extends from the back of the therapy module 11 and one securement recess 54 is defined in the module seat 50. Also, one securement recess 54 is defined in the back of the therapy module 11 and one securement protrusion extends from the module seat 50. In a preferred embodiment, at least one of the securement protrusions and at least one of the securement recess include one or more magnet members 52 associated therewith that are magnetically attracted to one another, that help secure the ring module 18 (or other therapy module 11) onto the module seat 50 and the vibration therapy device 12. One, two or more magnet members can be included. The magnet members 52 are located within the housing of the therapy module and with the housing of the head portion. One or more magnet members 52 can also be located at other positions around the module seat 50 and the back of the therapy module 11.

In a preferred embodiment, the system includes an electrical connection system 58 between the vibration therapy device 12 and the therapy module 11. In a preferred embodiment, the therapy module 11 includes male electrical contacts 60 extending therefrom (see FIGS. 6 and 10) and the module seat 50 includes complementary female electrical contacts 62. Power is supplied from the battery 20, through the male and female electrical contacts and to the LEDs or other powered components. It will be appreciated that the male and female electrical contacts can be reversed. In a preferred embodiment, the male or female electrical contacts are associated with one of the securement recesses 54 and one of the securement protrusions 48. In the embodiment shown in the drawings, the securement protrusion 48 that extends from the back of the therapy module 11 is a magnetic securement protrusion and the securement recess 54 that is defined in the module seat 50 is a magnetic securement recess. Furthermore, the securement recess 54 that is defined in the back of the therapy module 11 is an electrical securement recess (and includes male electrical contacts) and the securement protrusion 48 that extends from the module seat 50 is an electrical securement protrusion (and includes female electrical contacts).

As shown in FIG. 1, in a preferred embodiment, the handle portion 14 forms an angle of about 120 degrees with the reciprocating shaft 24 to avoid blocking the user's view during treatment. Anywhere between 90 degrees and 180 degrees is within the scope of the invention. In another embodiment, the head portion can be rotatable and/or pivotable and/or swivelable with respect to the handle portion 14.

Figure 8:
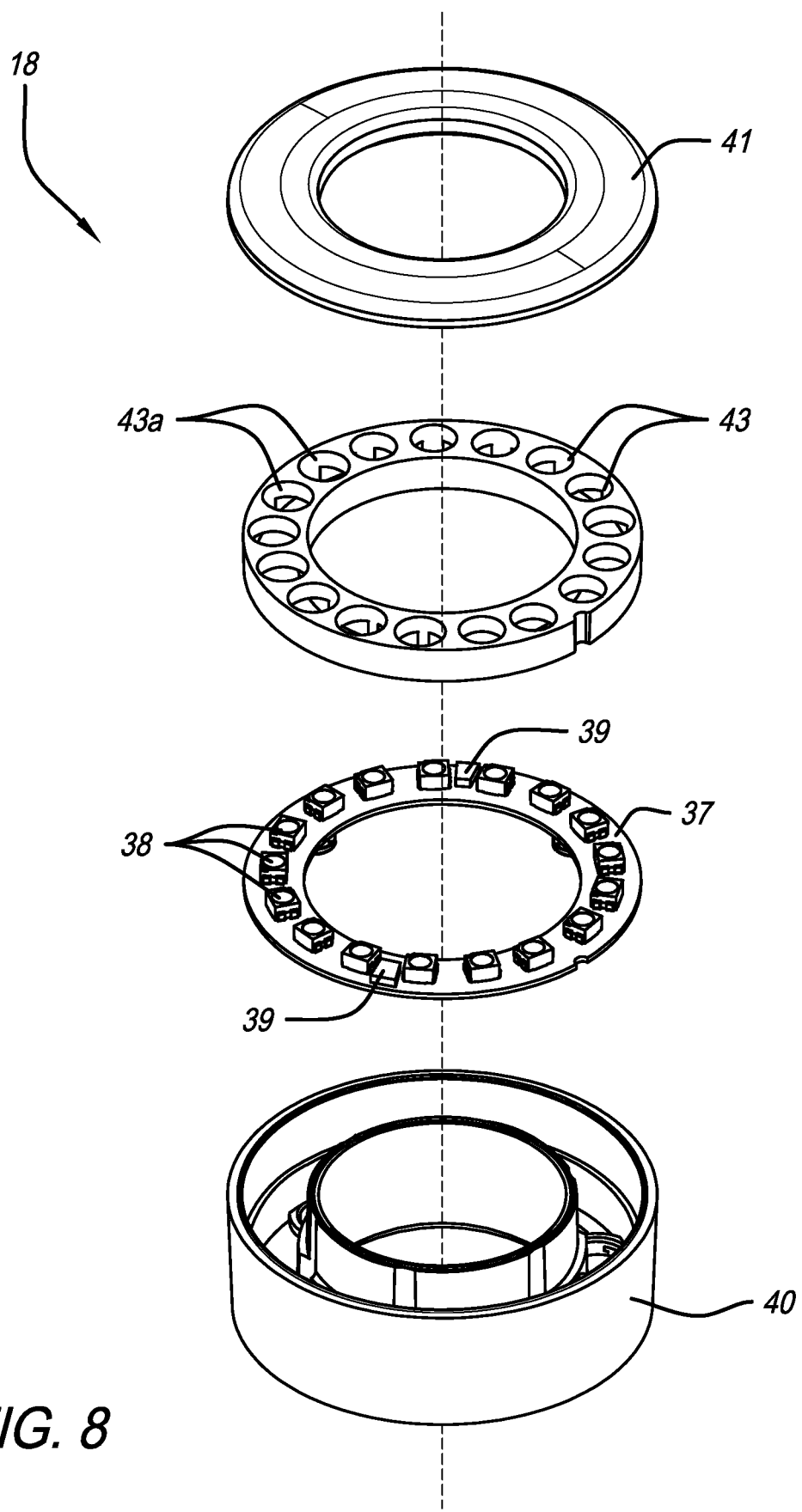
FIG. 8 is an exploded perspective view of the light ring module.

FIG. 8 shows the components of the light ring module 18 including the printed circuit board 37 including the LEDs 38 and proximity sensors 39. In a preferred embodiment, the proximity sensors 39 are positioned approximately 180° from another. With respect to 180°, approximately means within 10°. However, they can be positioned anywhere around the ring. The proximity sensors 39 are provided so that LED lights in the light module only turn on (or go from dimmed to "treatment level" or off to "treatment level") when they are less than a predetermined distance from or the lens is in contact with the user's face or skin. In a preferred embodiment, one proximity sensor 39 is located at about twelve o'clock on the PCB and the other is located at about six o'clock. In use, after activating the light ring module, the lights remain off or in a dimmed state until the front surface of the module is placed within a predetermined distance of the user's face, at which point the lights brighten to a treatment level (where the lights will be effective for the desired treatment—e.g., red LED treatment, blue LED treatment or infrared). Preferably, the proximity sensors are programmed such that they only determine the proximity at intervals or at a predetermined frequency (e.g., every one second) so that the lights are not turning on and off every time the device is pulled away from the face or angled during use on the face such that the proximity sensor is out of range. Any type of proximity sensor can be used. In a preferred embodiment, the proximity sensor emits a beam that is reflected by the user's face. The sensor determines the distance with the face based on the time (or frequency) for the beam returning from the user's skin after reflection. It will be appreciated that by having two proximity sensors 180° apart, as long as one is within the predetermined range of distance from the skin (operating surface), the lights will not dim or turn off (or go to a point that is less than the desired treatment level or intensity of the lights).

As shown in FIG. 8, in a preferred embodiment, the light ring module includes a housing portion 40, PCB 37, cover or lens 41 and a light direction member 42 that includes a plurality of openings 43 defined therein. The openings 43 are each aligned with an LED 38 and provide a tunnel so that the light beams emitted from each of the LEDs are directed generally parallel to one another and, therefore, generally perpendicular to the cover 41 and the user's skin as the device is used. This helps prevent the light from shining outwardly and into the user's eyes during use. The ring module includes the central opening 18a and an outer surface 41a. As shown in FIG. 5, in a preferred embodiment, the contact surface 19c of the reciprocating attachment 19 extends further from the module seat 50 than the outer surface 41a of the ring module 18. Other types of ring modules with other therapies are in the scope of the present invention.

Figure 9:
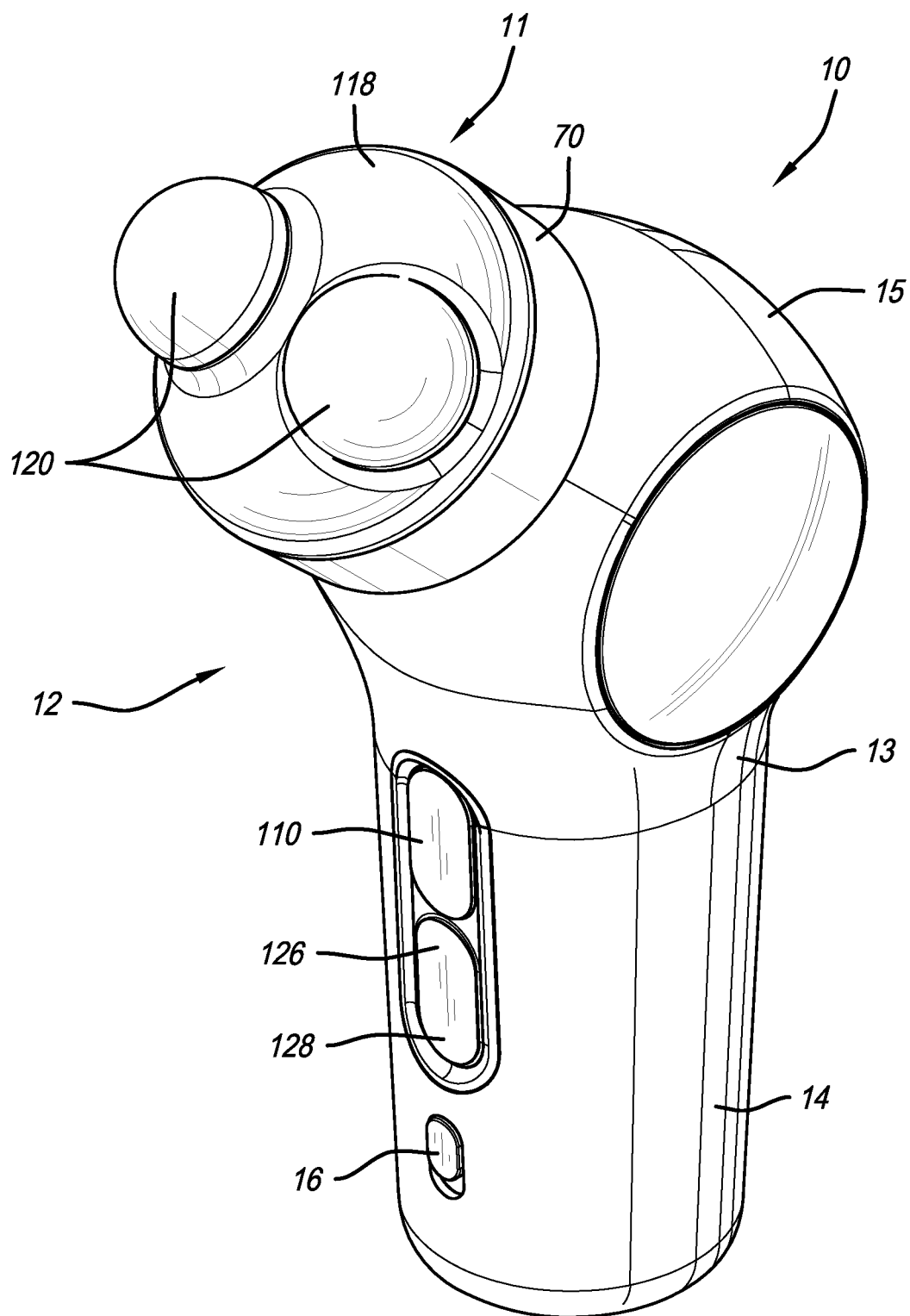
FIG. 9 is a perspective view of the vibration therapy device with the micro-current cap module thereon.
Figure 10:
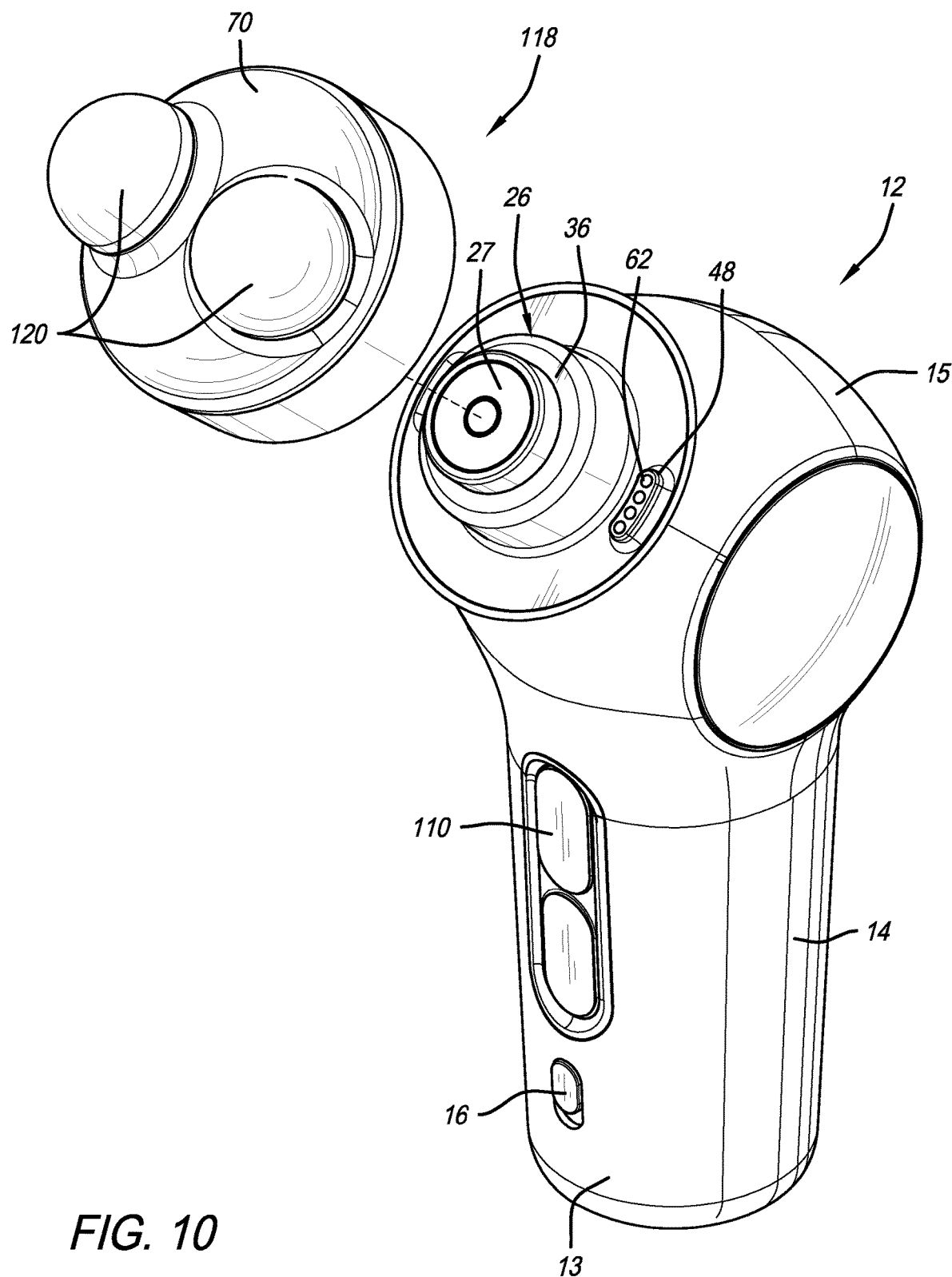
FIG. 10 is a perspective view of the vibration therapy device with the micro-current cap module exploded therefrom.
Figure 11:
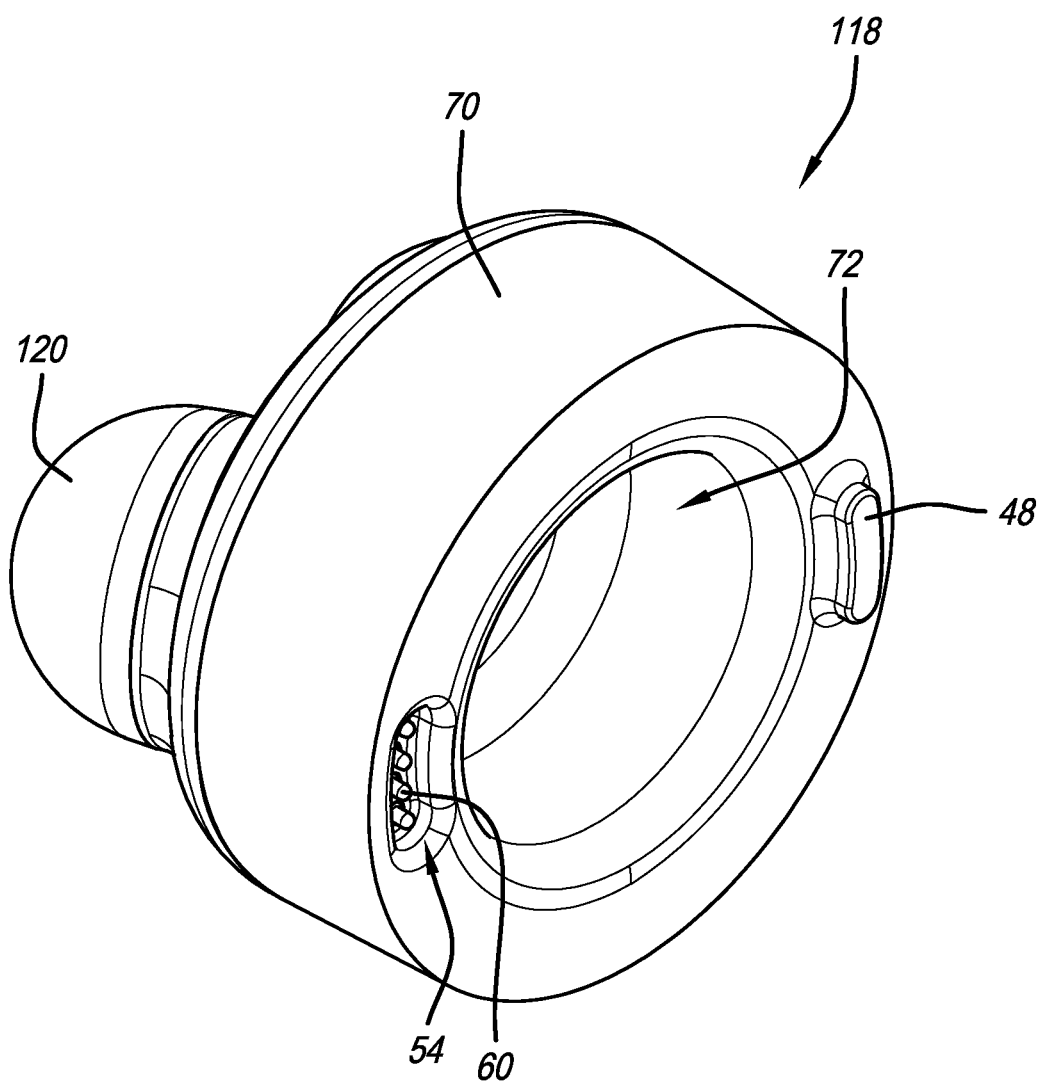
FIG. 11 is a rear perspective view of a micro-current cap module.

FIGS. 9-11 show another type of therapy module 11 referred to generally herein as a cap module and more specifically (for this particular module) as a micro-current cap module 118 that covers the magnet seat 26b of the attachment member 26. The micro-current cap module 118 includes a main body portion 70 and a rear recess 72 defined therein that receives the attachment member 26 when the micro-current cap module 118 is fitted on the module seat 50. The micro-current cap module 118 shown in FIGS. 9-11 includes micro-current therapy. However, different cap modules can include other therapies. Micro-current therapy can also be included in a ring module. The micro-current cap module 118 includes first and second terminals or an anode and cathode 120. This module includes an electrical connection and magnetic attraction just like the ring module 18 described above. As will be appreciated by those of ordinary skill in the art, when the anode and cathode 120 are placed against a user's skin, an electrical connection is created and micro-current is transmitted into the user's skin to provide micro-current treatment.

Figure 12:
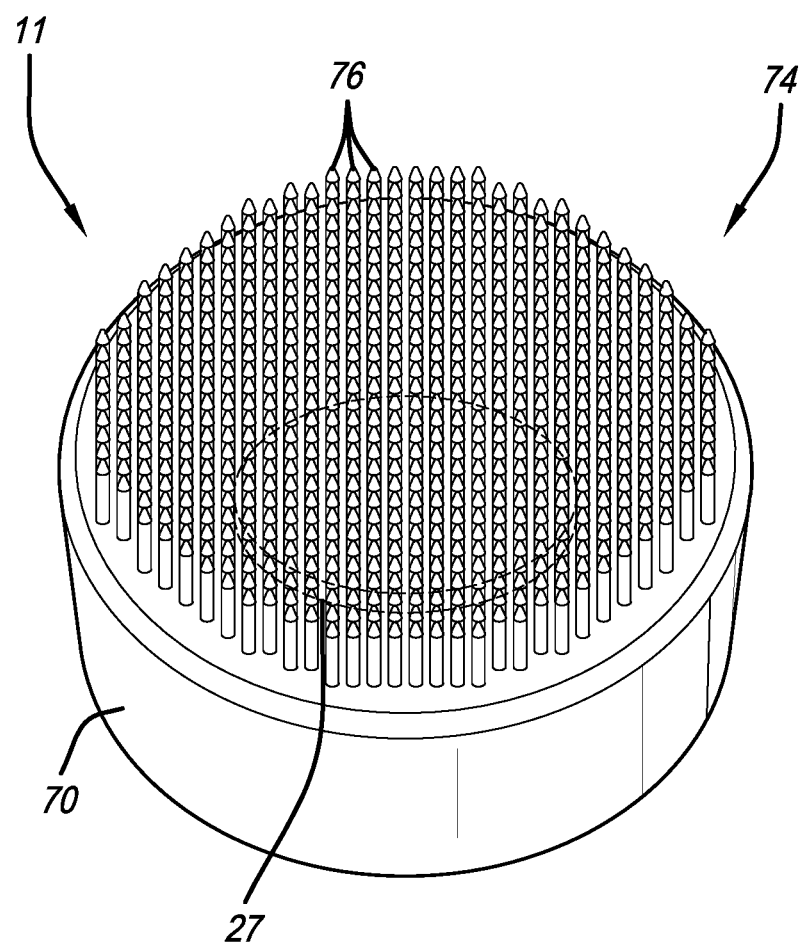
FIG. 12 is a perspective view of the vibration therapy device with the cleansing cap module exploded therefrom.
Figure 13:
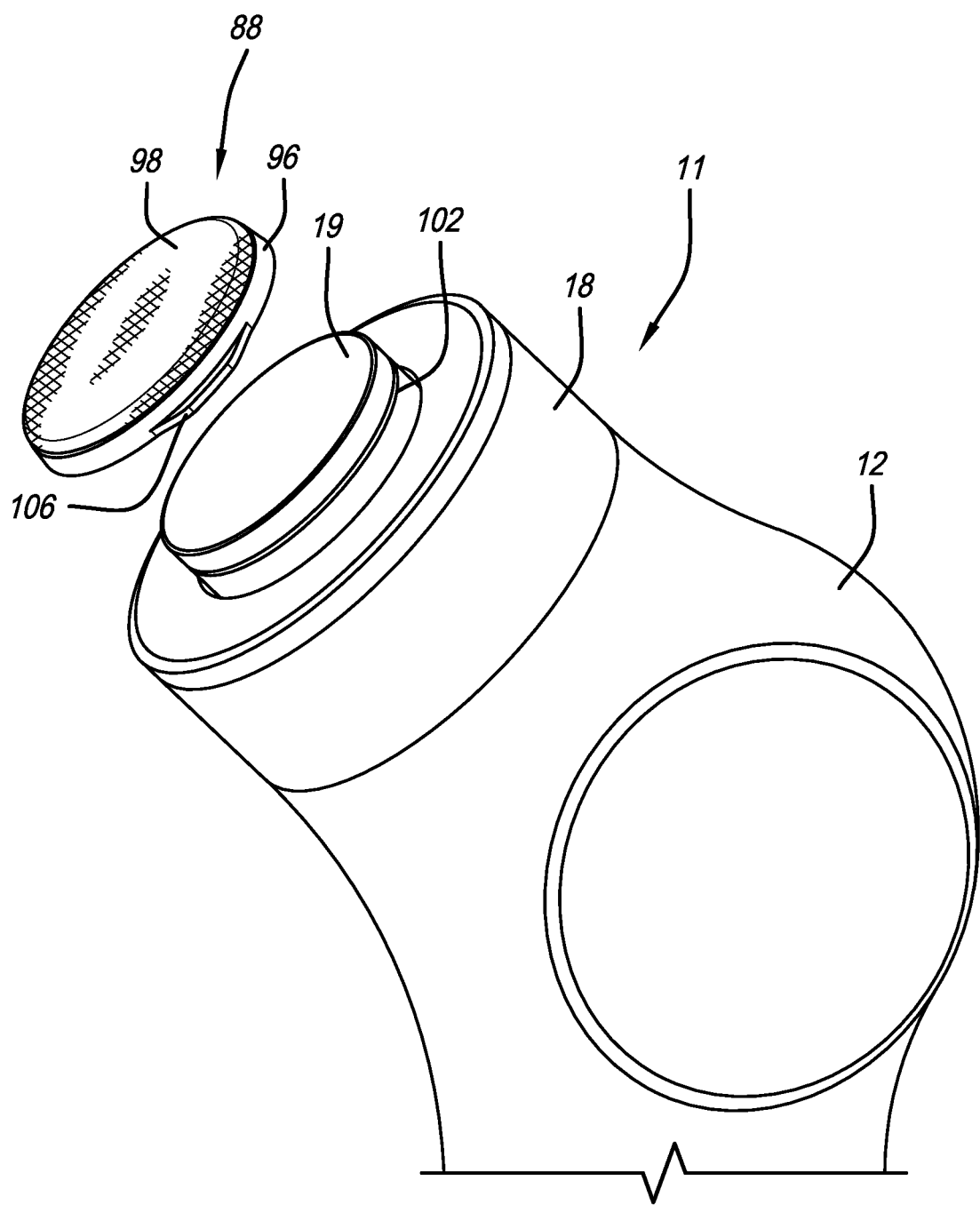
FIG. 13 is a perspective view of the vibration therapy device with a treatment member exploded therefrom.
Figure 14:
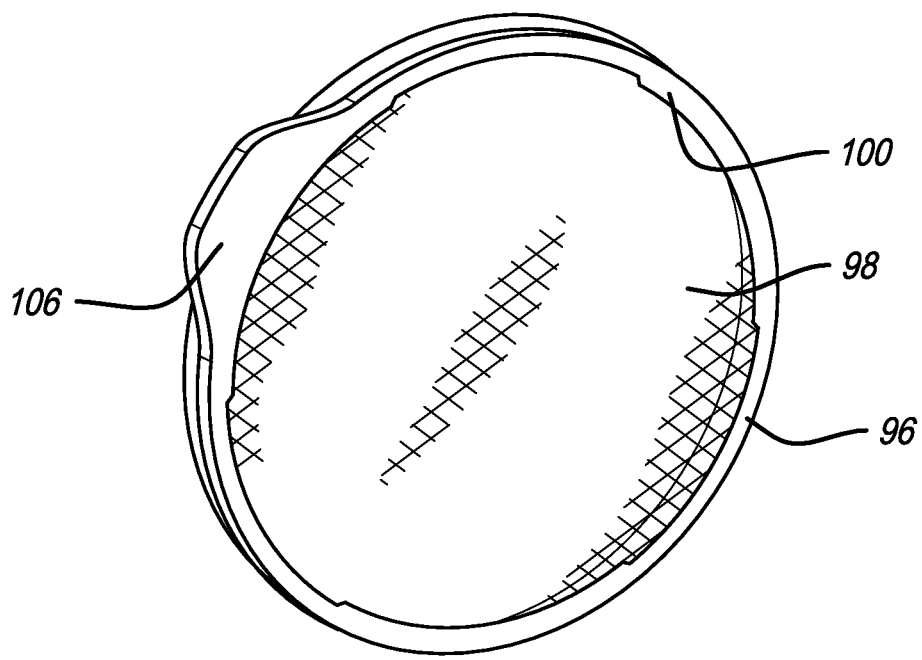
FIG. 14 is a perspective view of the therapy member.
Figure 15:
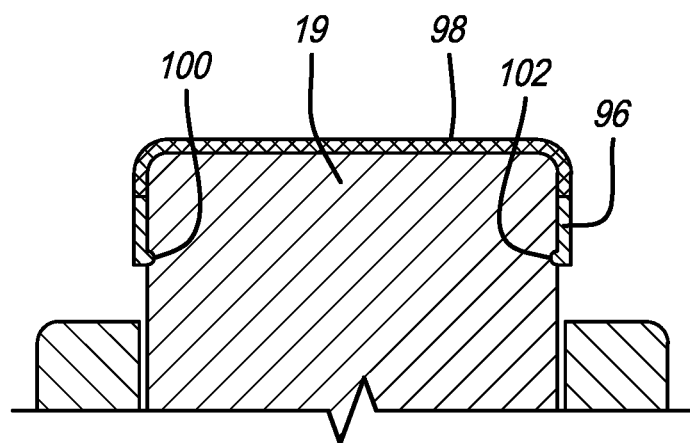
FIG. 15 is a cross-sectional view of the therapy member on the reciprocating attachment.
Figure 16:
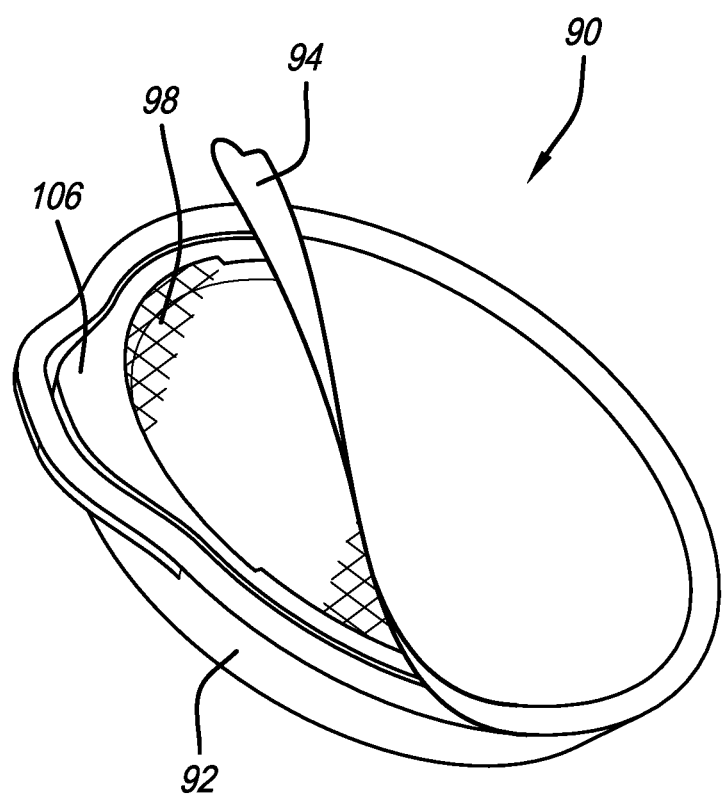
FIG. 16 is a perspective view of the therapy member in packaging with the lid partially peeled back.

FIG. 12 shows another type of cap module referred to herein as a cleansing cap module 74 that includes a plurality of bristles 76 thereon. The cleansing cap module 74 includes a main body portion 70 and recess that receives the attachment member 26 when the cleansing cap module 74 is fitted on the module seat 50. The cleansing cap module 74 may also include (but preferably does not include) an electrical connection just like the ring module 18 described above. The cleansing cap module 74 preferably also includes a magnet 27 therein that is magnetically attracted to and connects to the magnet 27 in the attachment member 26. As a result, in use, the cleansing cap module 74 reciprocates against the user's skin. In a preferred embodiment, the main body portion 70 preferably includes the complementary securement protrusions and recesses, like the other therapy modules 11. Therefore, the cleansing cap module is configured to be removable secured to both the attachment member 26 (e.g., via magnets) and to the module seat 50 (e.g., via the complementary securement protrusions and recesses and/or magnet members). However, the complementary securement protrusions and recesses can also be omitted since connected is made between the central magnet 27 and the magnet in the attachment member 26. A cleansing formulation can be placed on the bristles 76 during use.

FIGS. 13-16 show a preferred embodiment system for attaching a component with microfiber material thereon (referred to herein as a skin treatment member 88) to the reciprocating attachment 19. In a preferred embodiment, the skin treatment member 88 includes lotion or some type of skin treatment ointment or fluid thereon and, therefore, is packaged in a pod member 90 that includes a container portion 92 and a lid 94. In a preferred embodiment, the skin treatment member 88 includes a generally ring shaped main body portion 96 and a delivery portion 98 that is preferably made of microfiber and includes the lotion thereon.

In a preferred embodiment, the skin treatment member 88 is attachable or securable to the reciprocating attachment 19. Preferably, the main body portion 96 includes one or more ridge members 100 on the inside surface thereof and extending inwardly that are received in one or more grooves 102 defined in the outer surface of the reciprocating attachment 19. The skin treatment member 88 preferably also includes a handle or tab 106 extending from the main body portion 96 that aids with attachment and removal of the skin treatment member 88 from the reciprocating attachment 19. In use, the skin treatment member 88 is removed from the pod member 90 (by peeling back the lid 94) and the treatment member is placed or seated on the reciprocating attachment 19. It will be appreciated that the main body portion 96 is made of a flexible material (such as plastic) so the ridge members 100 flex over the reciprocating attachment 19 and snap into the groove 102 on the outer surface of the reciprocating attachment. The delivery portion stretches across or spans the top or outer contact surface of the reciprocating attachment 19.

The delivery portion 98 is then placed against the user's face and the device is activated such that the reciprocating attachment 19 (also referred to herein as a mallet) with the treatment member 88 thereon vibrates or percusses against the user's skin. After user, the use can pull on the tab 106 to separate the treatment member 88 from the mallet 19. As shown in FIG. 11, the skin treatment member 88 can be placed on the mallet 19 when the ring module 18 is on the device. Therefore, the LED light therapy can be used simultaneously with the vibration therapy and the treatment member therapy. The groove 102 is preferably located further from the module seat 50 than the outer surface 41a or outside of the ring module so that the skin treatment member 88 secured in the groove can reciprocate outside of the ring module.

Figure 17C:
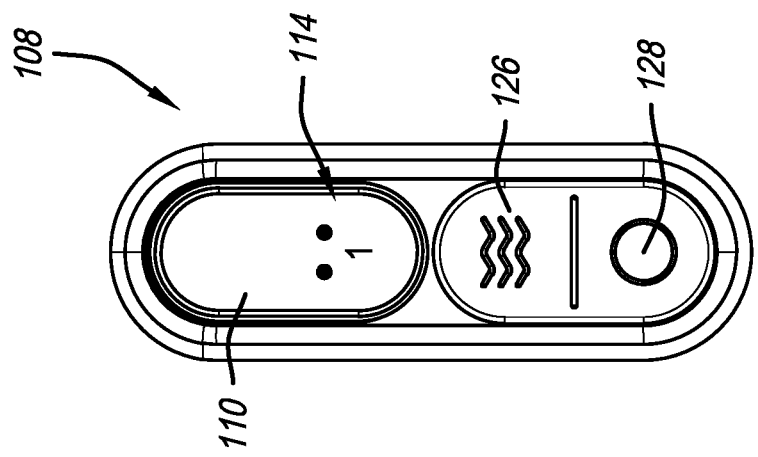
FIG. 17C is a view showing the user interface and display with the micro-current cap module symbol illuminated.
Figure 17B:
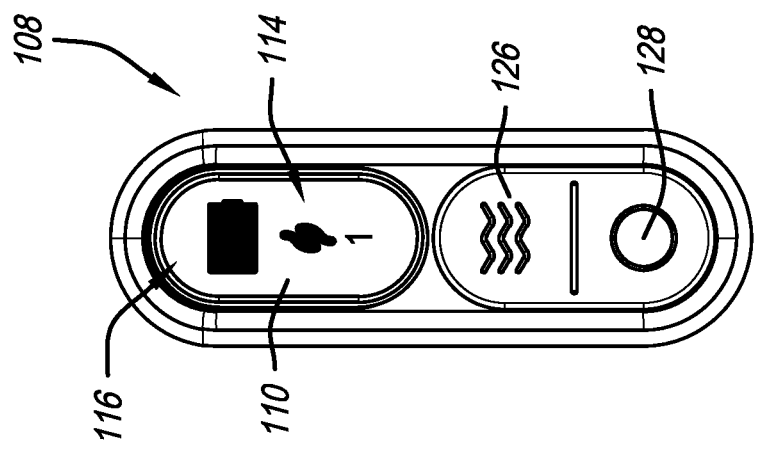
FIG. 17B is a view showing the user interface and display with the heat ring module symbol and battery symbol illuminated.
Figure 17A:
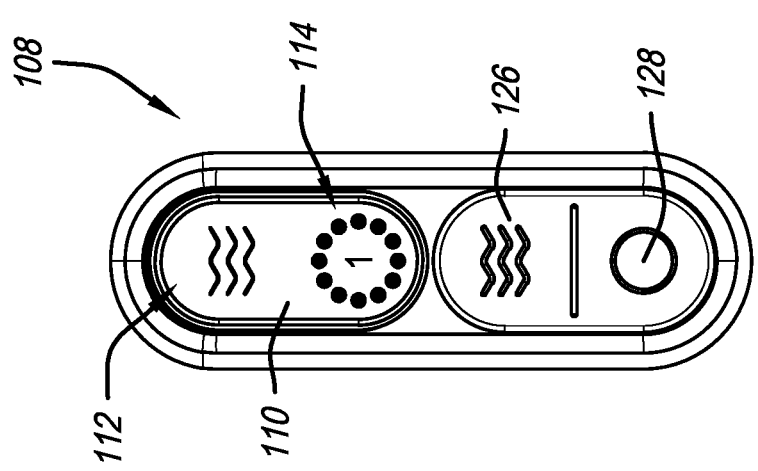
FIG. 17A is a view showing the user interface and display with the light ring module symbol and vibration symbol illuminated.

FIGS. 17A-17C show a control center 108 (or user interface—UI) that includes a display screen 110 and one or more buttons and/or switches that can be used for controlling the device 12 and the various therapy modules 11. The buttons can control different modes, different intensities, etc. In a preferred embodiment, the control center includes display screen 110, motor toggle button 126 (for toggling through different frequencies or speeds for the attachment member 26 and any reciprocating attachment thereon), module toggle button 128 (for toggling through different intensities or options for the therapy modules electrically connected to the device) and a power switch 16. FIG. 17A shows the display screen 110 with the motor speed level 112 at the top and the therapy module level 114 (with the light ring module symbol thereon) at the bottom. FIG. 17B shows the display screen 110 with the battery level 116 at the top and the therapy module level 114 (with the heat ring module symbol thereon) at the bottom. FIG. 17C shows the display screen 110 with nothing on the top and the therapy module level 114 (with the micro-current symbol thereon) at the bottom. Other symbols and the like that can be shown in the display screen include Bluetooth. It will be appreciated that the control center 108 is in data communication with the controller and associated components for controlling the device 12. Preferably, the device can sense or determine what type of therapy module has been seated on an electrically connected to the device. This allows the module toggle button 128 to toggle through the modes of the proper module and for the proper therapy module level to be displayed on display 110. Furthermore, in use, when a cap module (e.g., micro-current module 118) is seated on the module seat and electrically connected to the device, the motor is not activated (to reciprocate the attachment member) because the attachment member and magnet seat is located inside the cap module. When a ring module is seated on the device, the motor can be activated so that the reciprocating attachment can reciprocate within the central opening of the ring module.

It will be appreciated that all or some of the components discussed herein can be contained, sold or distributed in a kit. In other words, the vibration therapy system can be provided to users as a kit (e.g., within a case, box, bag or the like). The kit can include the vibration therapy device, one or more reciprocating attachments and one or more therapy modules. For example, an exemplary kit includes the device, the light ring module, the micro-current cap module, the reciprocating attachment with the groove therearound a and charger all within a case or container.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges.

Although the operations of any method(s) disclosed or described herein either explicitly or implicitly are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

The teachings of the disclosure provided herein can be applied to other systems, not necessarily the system described above. The elements and acts of the various embodiments described above can be combined to provide further embodiments. Any measurements or dimensions described or used herein are merely exemplary and not a limitation on the present invention. Other measurements or dimensions are within the scope of the invention.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will include the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A vibration therapy device comprising:
   a housing that includes a handle portion, a head portion and a module seat defined on the head portion,
   an electrical source,
   a motor positioned in the housing,
   a switch for activating the motor,
   a push rod assembly operatively connected to the motor, wherein a reciprocating attachment is removably received on a distal end of the push rod assembly, wherein the reciprocating attachment defines a reciprocating attachment diameter, and
   a ring module removably secured to the module seat, wherein the ring module provides first type of therapy and is in electrical communication with the electrical source, wherein the ring module includes a central opening that defines a central opening diameter, wherein the central opening diameter is larger than the reciprocating attachment diameter, such that the reciprocating attachment is configured to reciprocate within and relative to the ring module.

2. The vibration therapy device of claim 1 wherein the module seat includes a first electrical connector, and wherein the ring module includes a second electrical connector in electrical communication with the first electrical connector.

3. The vibration therapy device of claim 1 wherein the ring module includes an outer surface, wherein the reciprocating attachment includes a contact surface, wherein the contact surface of the reciprocating attachment extends further from the module seat than the outer surface of the ring module.

4. The vibration therapy device of claim 3 wherein a skin treatment member that includes a delivery portion is removably secured to the reciprocating attachment, and wherein the delivery portion at least partially covers the contact surface.

5. The vibration therapy device of claim 3 wherein the ring module includes a plurality of LED's therein, wherein the LEDs are configured to operate at a treatment level only when the outer surface is less than a predetermined distance from an operating surface.

6. The vibration therapy device of claim 5 wherein the ring module further comprises at least first and second proximity sensors that are positioned approximately 180° from one another within the ring module, wherein the first and second proximity sensors are each configured to activate the LEDs at the treatment level when the outer surface of the ring module is less than the predetermined distance from the operating surface.

7. The vibration therapy device of claim 1 wherein the ring module can be removed from the module seat while the reciprocating attachment is received on the distal end of the push rod assembly.

8. The vibration therapy device of claim 1 wherein the housing includes a protrusive portion that extends into the central opening of the ring module, and wherein at least a portion of the push rod assembly extends through the protrusive portion.

9. A vibration therapy system comprising:
   a vibration therapy device that includes
      a housing that includes a handle portion, a head portion and a module seat defined on the head portion,
      an electrical source,
      a motor positioned in the housing,
      a switch for activating the motor, and
      a push rod assembly operatively connected to the motor, wherein the push rod assembly includes an attachment member that defines the distal end of the push rod assembly,
   a ring module that includes a central opening and that is configured to be removably secured to the module seat, wherein the ring module provides a first type of therapy and is in electrical communication with electrical source, wherein when the ring module is removably secured to the module seat, the distal end of the push rod assembly extends into the central opening,
   a cap module that includes a main body portion and a rear recess and that is configured to be removably secured to the module seat, wherein when the cap module is removably secured to the module seat, the distal end of the push rod assembly extends into the rear recess and the cap module is electrically communicated with the electrical source, and
   a reciprocating attachment that is configured to be removably received on the attachment member, wherein when the ring module is received on the module seat, the reciprocating attachment extends through the central opening.

10. The vibration therapy system of claim 9 further comprising a skin treatment member that is configured to be removably secured to the reciprocating attachment, wherein the skin treatment member includes a delivery portion that is configured to at least partially cover a contact surface of the reciprocating attachment.

11. The vibration therapy system of claim 9 wherein when the ring module is received on the module seat the motor can be activated to reciprocate the attachment member, and wherein when the cap module is received on the module seat and is electrically communicated with the electrical source, the motor cannot be activated to reciprocate the attachment member.

12. The vibration therapy system of claim 9 wherein the cap module is configured to be removably secured to the module seat and the attachment member.

13. The vibration therapy system of claim 9 wherein the reciprocating attachment defines a reciprocating attachment diameter, wherein the central opening defines a central opening diameter, and wherein the central opening diameter is larger than the reciprocating attachment diameter, such that the reciprocating attachment can reciprocate within and relative to the ring module.

14. The vibration therapy system of claim 9 wherein the cap module provides a second type of therapy.

15. A vibration therapy device comprising:
- a housing that includes a handle portion, a head portion and a module seat defined on the head portion,
- an electrical source,
- a motor positioned in the housing,
- a switch for activating the motor,
- a push rod assembly operatively connected to the motor,
- a reciprocating attachment removably secured to a distal end of the push rod assembly, wherein the reciprocating attachment defines a reciprocating attachment diameter and is removable from the distal end of the push rod assembly by a user, wherein the reciprocating attachment includes a contact surface, wherein a skin treatment member that includes a delivery portion is removably secured to the reciprocating attachment, wherein the delivery portion at least partially covers the contact surface, wherein the skin treatment member is removable from the reciprocating attachment by a user, and a ring module removably secured to the module seat, wherein the ring module provides a first type of therapy and is in electrical communication with the electrical source, wherein the ring module includes a central opening that defines a central opening diameter, wherein the central opening diameter is larger than the reciprocating attachment diameter, such that the reciprocating attachment is configured to reciprocate within and relative to the ring module.

16. The vibration therapy device of claim 15 wherein the reciprocating attachment includes a groove defined therein, wherein at least a portion of the skin treatment member is received in the groove.

17. The vibration therapy device of claim 16 wherein the skin treatment member includes a main body portion that, together with the delivery portion, defines an attachment recess, wherein at least one ridge member extends inwardly from the main body portion into the attachment recess and is received in the groove on the reciprocating attachment.

18. The vibration therapy device of claim 15 wherein the delivery portion includes a lotion therein.

19. The vibration therapy device of claim 15 wherein the delivery portion comprises a microfiber material.

20. The vibration therapy device of claim 19 wherein the microfiber material includes a lotion therein.

* * * * *